(12) United States Patent
Quintero et al.

(10) Patent No.: US 7,306,390 B2
(45) Date of Patent: Dec. 11, 2007

(54) APPLICATORS, DISPENSERS AND METHODS FOR DISPENSING AND APPLYING ADHESIVE MATERIAL

(75) Inventors: Julian A. Quintero, Raleigh, NC (US); Jerry Y. Jonn, Raleigh, NC (US); Jack Goodman, Ann Arbor, MI (US); Daniel L. Hedgpeth, Raleigh, NC (US); William M. Cotter, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 198 days.

(21) Appl. No.: 10/663,909

(22) Filed: Sep. 17, 2003

(65) Prior Publication Data

US 2005/0175395 A1 Aug. 11, 2005

Related U.S. Application Data

(63) Continuation-in-part of application No. 10/359,699, filed on Feb. 7, 2003, now abandoned.

(51) Int. Cl.
*B43K 5/14* (2006.01)

(52) U.S. Cl. .................. 401/133; 401/134; 401/132; 401/196

(58) Field of Classification Search ........ 401/132–135, 401/196, 194; 604/3; 222/81–86, 88–90
See application file for complete search history.

(56) References Cited

U.S. PATENT DOCUMENTS

| | | | |
|---|---|---|---|
| D145,586 S | 9/1946 | Reynolds | D19/48 |
| D155,031 S | 8/1949 | Patterson | D9/338 |
| 4,543,005 A | 9/1985 | Kuboshima | 401/260 |
| 4,581,021 A | 4/1986 | Landau et al. | 604/212 |
| 4,640,637 A | 2/1987 | Winthrop | 401/101 |
| 4,784,506 A | 11/1988 | Koreska et al. | |
| 4,813,870 A | 3/1989 | Pitzen et al. | 433/90 |
| 4,960,340 A | 10/1990 | Tamiya et al. | 401/186 |
| 5,193,928 A * | 3/1993 | Balzer et al. | 401/132 |
| 5,358,349 A | 10/1994 | Burroughs et al. | 401/184 |
| D443,303 S | 6/2001 | Ashe | D19/48 |
| 6,328,715 B1 | 12/2001 | Dragan et al. | 604/232 |
| 6,425,704 B2 | 7/2002 | Voiers et al. | 401/196 |
| 6,447,476 B1 | 9/2002 | Sogaro | 604/85 |

(Continued)

FOREIGN PATENT DOCUMENTS

GB    2 001 285    1/1979

(Continued)

*Primary Examiner*—Khoa D. Huynh

(57) ABSTRACT

An applicator/dispenser assembly for dispensing and/or applying an adhesive material comprises: a first body portion and a second body portion, at least one of the first and second body portions being movable relative to the other of the first and second body portions; a cavity in at least one of the first and second body portions; and a piercing or breaking member arranged on one of the first and second body portions. Movement of one of the first and second body portions relative to the other of the first and second body portions moves the piercing or breaking member into the cavity. When a container of adhesive material is at least partially disposed within the cavity, movement of one of the first and second body portions relative to the other moves the piercing or breaking member to rupture the container for dispensing and/or applying the adhesive material.

44 Claims, 16 Drawing Sheets

U.S. PATENT DOCUMENTS

| | | |
|---|---|---|
| D471,586 S | 3/2003 | Geiselhart et al. .............. D19/36 |
| 6,536,975 B1 * | 3/2003 | Tufts ............................ 401/134 |
| D472,578 S | 4/2003 | Plantz et al. .................. D19/51 |
| 6,705,790 B2 * | 3/2004 | Quintero et al. .............. 401/132 |
| 6,729,786 B1 * | 5/2004 | Tufts et al. ................... 401/133 |
| 6,915,901 B2 * | 7/2005 | Feinberg et al. .............. 206/363 |
| 6,991,394 B2 * | 1/2006 | Tufts et al. ................... 401/134 |
| 2002/0076255 A1 * | 6/2002 | Hoang et al. ................. 401/133 |

FOREIGN PATENT DOCUMENTS

| | | |
|---|---|---|
| WO | WO01/51360 | 7/2001 |

* cited by examiner

APPLICATORS, DISPENSERS AND METHODS FOR DISPENSING AND APPLYING ADHESIVE MATERIAL

RELATED APPLICATION INFORMATION

This application is a Continuation-In-Part of U.S. patent application Ser. No. 10/359,699 filed Feb. 7, 2003 now abandoned, the entire disclosure thereof being incorporated herein by reference.

BACKGROUND OF THE INVENTION

This invention relates to applicators and/or dispensers for dispensing and/or applying an adhesive material, for example, a polymerizable monomer compound such as a cyanoacrylate adhesive, particularly for medical use.

Numerous swabs, applicators, dispensers and kits for dispensing and applying various materials, including adhesive materials, are known. However, these known arrangements possess various shortcomings that make them undesirable in many applications.

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

Medical applications of 1,1-disubstituted ethylene monomer adhesive compositions include use as an alternate or an adjunct to surgical sutures and staples in wound closure as well as for covering and protecting tissue wounds such as lacerations, abrasions, burns, stomatitis, sores, and other open surface wounds. When such an adhesive is applied, it is usually applied in its monomeric form, and the resultant polymerization gives rise to the desired adhesive bond.

Applicators for dispensing a polymerizable and/or cross-linkable material, such as a 1,1-disubstituted ethylene formulation, are disclosed in U.S. Pat. No. 5,928,611 to Leung and copending U.S. patent application Ser. No. 09/430,177, filed Oct. 29, 1999. In general, many different 1,1-disubstituted ethylene formulations are known for various applications, for example, cyanoacrylate formulations used as fast-acting surgical adhesives, sealants, bioactive agent release matrixes and implants utilized in medical, surgical and other in vivo applications. Such formulations include those disclosed by Leung and the references cited therein.

However, due to the need to apply the adhesive in its monomeric form, and due to the rapid polymerization rate of the monomers, it has been very difficult to design effective and commercially viable applicators and/or dispensers. Such applicators and/or dispensers must counterbalance the competing requirements that the monomer not prematurely polymerize, that the monomer be easily applied, that the monomer polymerize at a desired rate upon application, and that the sanitary and/or sterile properties of the monomer and applicator—whether real or perceived—be maintained. This latter requirement, that the actual or perceived sanitary and sterile condition of the monomer and applicator be maintained, is particularly important in medical applications, where the user and/or the patient desires a clean product so as not to introduce further bacteria or foreign matter into a wound site.

A further problem in addressing the above requirements of adhesive applicators and/or dispensers is the need to provide a stable monomer product. Particularly in small quantities, cyanoacrylate monomers are prone to premature polymerization, which would render the product useless. Thus, industrial production of monomeric adhesive compositions has had to balance rapid cure rates and high bond strengths with shelf-life. The shelf-life of these adhesives is primarily related to stability (i.e., constancy of compositional nature), uncured physical properties, rate of cure of the adhesive, as well as final cured properties of the composition. For example, the shelf-life of a monomeric α-cyanoacrylate composition may be measured as a function of the amount of time the composition can be stored before unacceptable levels of polymerization, such as measured by viscosity increase, occur. Unacceptable levels are indicated by a level of polymerization product that reduces the usefulness of the composition in the application for which it is produced.

Known devices fail to provide an applicator and/or dispenser that is optimized for convenient dispensing and application of adhesive materials on a variety of surfaces and structures. The known applicators are generally either optimized for delivery of other compositions or are inconvenient for use in conjunction with adhesives. Furthermore, such conventional devices generally do not address the competing needs of ease of use and adhesive stability prior to application.

SUMMARY OF THE INVENTION

This invention addresses the above needs by providing applicators and dispensers that permit economical and efficient use of adhesive compositions. In embodiments of this invention, applicators and/or dispensers are provided that are more user friendly. In embodiments of this invention, applicators and/or dispensers are provided that are more ergonomic. In embodiments of this invention, applicators and/or dispensers are provided whereby an amount of adhesive material may be conveniently applied. The applicators and/or dispensers can be either disposable or reusable, depending on the desired application.

In embodiments, an applicator and/or dispenser is designed to facilitate manipulation by hand for dispensing and/or applying an adhesive. For example, in embodiments of this invention, applicators and/or dispensers are provided that are pen-like, providing a familiar feel to the user. In embodiments, an applicator and/or dispenser is designed to be more comfortable to the user, easier to grip and/or easier to operate.

In embodiments, an applicator and/or dispenser is designed to provide acceptable stability and shelf-life to the adhesive composition without the need to add separate stabilizer materials to the polymerizable monomer. Thus, in these embodiments, because the shelf-life is provided by the applicator and/or dispenser itself, the cure rate of the adhesive composition is not adversely affected, as in the case where one or more stabilizers are added. Accordingly, the need to apply separate polymerization initiators or rate modifiers can be reduced or even eliminated.

In other embodiments, an applicator and/or dispenser includes a polymerization initiator or accelerator for the adhesive material. The polymerization initiator or accelerator may be disposed in or on a tip or other part of the applicator. The polymerization initiator or accelerator may be absorbed or adsorbed into a porous portion of the applicator, may be coated on a surface of the applicator, or otherwise incorporated into a portion of the applicator. The applicator and/or dispenser may also include a frangible barrier separating first and second compartments, for example, to keep the polymerization initiator or accelerator separated from the adhesive material prior to use.

In particular, this invention is directed to an applicator/dispenser for dispensing and/or applying an adhesive material, comprising: a first body portion and a second body portion, at least one of the first and second body portions being movable relative to the other of the first and second body portions; a cavity in at least one of the first and second body portions; and a piercing or breaking member arranged on one of the first and second body portions, wherein movement of one of the first and second body portions relative to the other of the first and second body portions moves the piercing or breaking member into the cavity. In various embodiments, the applicator/dispenser further comprises a container of adhesive material at least partially disposed within the cavity, wherein movement of one of the first and second body portions relative to the other of the first and second body portions moves the piercing or breaking member to rupture the container.

In embodiments, the adhesive material comprises a polymerizable monomer adhesive material. In embodiments, the adhesive material comprises a polymerizable 1,1-disubstituted ethylene monomer formulation. In still other embodiments, the adhesive material comprises a cyanoacrylate formulation.

In embodiments, an applicator/dispenser for a polymerizable monomeric adhesive material includes a material that provides acceptable stability and shelf-life to the adhesive composition without the need to add separate stabilizer materials to the polymerizable monomer. As noted above, because the shelf-life is provided by the material of the applicator and/or dispenser, the cure rate of the adhesive composition is not adversely affected. Thus, the need to apply separate polymerization initiators or rate modifiers can be reduced or even eliminated.

In other embodiments, the applicator/dispenser includes a polymerization initiator or accelerator for the adhesive material.

In embodiments, the applicator/dispenser further comprises a pivoting connection that movably connects the first and second body portions. In embodiments, the first and second body portions may comprise a handle portion of the applicator/dispenser.

In other embodiments, the second body portion is rotatable relative to the first body portion. In embodiments, the applicator/dispenser further comprises a camming surface arranged on one of the first and second body portions other than the one of the first and second body portions on which the piercing or breaking member is arranged, wherein rotation of the second body portion relative to the first body portion moves the piercing or breaking member into the cavity by contacting the camming surface and the piercing or breaking member.

In embodiments, the applicator/dispenser further comprises: a bladder disposed at least partially within the cavity, at least a portion of the bladder being flexible; and a container of adhesive material disposed within the bladder and at least partially located in the cavity, wherein movement of one of the first and second body portions relative to the other of the first and second body portions moves the piercing or breaking member to rupture the container. In embodiments, the applicator/dispenser further comprises a plug member at least partially disposed in an opening of the bladder, the plug member being made of a material that is at least one of porous, absorbent and adsorbent in nature. In embodiments, the plug member comprises an applicator tip.

In embodiments, the applicator/dispenser further comprises: a slide assembly having a plunger portion that is at least partially disposed in the cavity and a slide portion that is at least partially disposed outside the cavity, the slide assembly being slidably movable to move the plunger portion toward a dispensing opening of the cavity; and an opening in at least one of the first and second body portions through which the slide portion of the slide assembly extends. In embodiments, the applicator/dispenser further comprises: a container of adhesive material disposed in the cavity between the dispensing opening of the cavity and the plunger portion of the slide assembly, wherein movement of one of the first and second body portions relative to the other of the first and second body portions moves the piercing or breaking member to rupture the container and movement of the slide member moves the plunger portion to dispense the adhesive material from the cavity once the container is ruptured.

In other embodiments, this invention is directed to a kit comprising: at least one applicator/dispenser; and a plurality of containers of adhesive material arranged to be placed at least partially in the cavity of the at least one applicator/dispenser, wherein movement of one of the first and second body portions relative to the other of the first and second body portions moves the piercing or breaking member to rupture one of the containers that is placed at least partially in the cavity. In embodiments, the kit further comprises a plurality of removable applicator tips. In embodiments, the kit further comprises a polymerization initiator or rate modifier for the adhesive material. In embodiments, at least two of the plurality of containers contain different amounts of adhesive material. In other embodiments, at least two of the plurality of containers contain a different adhesive material.

In other embodiments, this invention is directed to a method of applying/dispensing an adhesive material comprising: placing a container of adhesive material at least partially into the cavity of an applicator/dispenser; moving one of the first and second body portions relative to the other of the first and second body portions to move the piercing or breaking member to rupture the container; and dispensing the adhesive material from the cavity. In embodiments, the method further comprises applying the dispensed adhesive to a substrate to be bonded.

Various other features and advantages of this invention will be apparent from the following detailed description of exemplary embodiments.

BRIEF DESCRIPTION OF THE DRAWINGS

Exemplary embodiments of this invention are described in detail below, with reference to the attached drawing figures, in which.

DETAILED DESCRIPTION OF EXEMPLARY EMBODIMENTS

In embodiments of this invention, an applicator/dispenser is provided that facilitates easy application of a desired quantity of polymerizable adhesive material. In embodiments, an amount of polymerizable adhesive material is prepackaged in the applicator dispenser in a frangible ampoule that is broken upon activation of the applicator/dispenser. The frangible ampoule may provide stability and/or shelf-life for the amount of polymerizable adhesive material.

Figure 1:
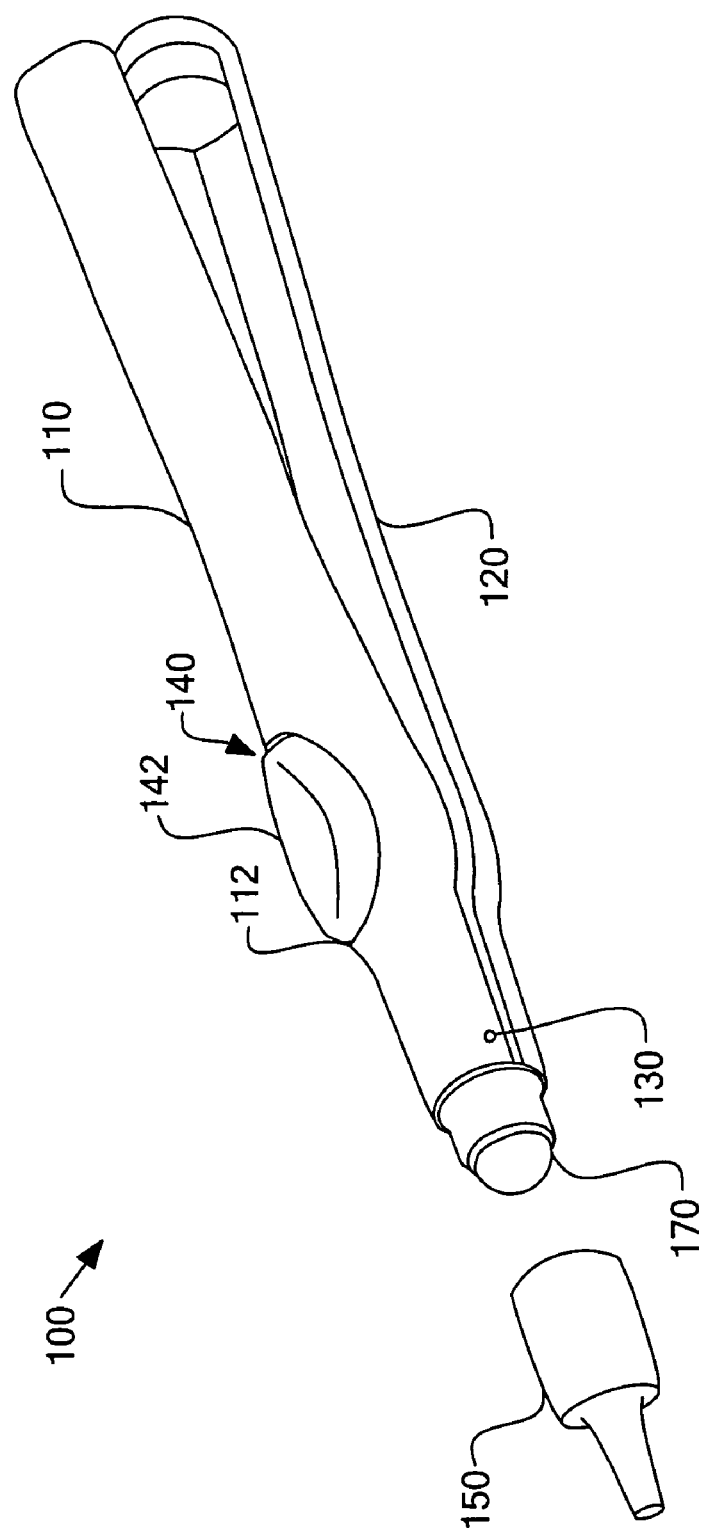
FIG. 1 is a perspective view of a first exemplary embodiment of this invention.
Figure 2:
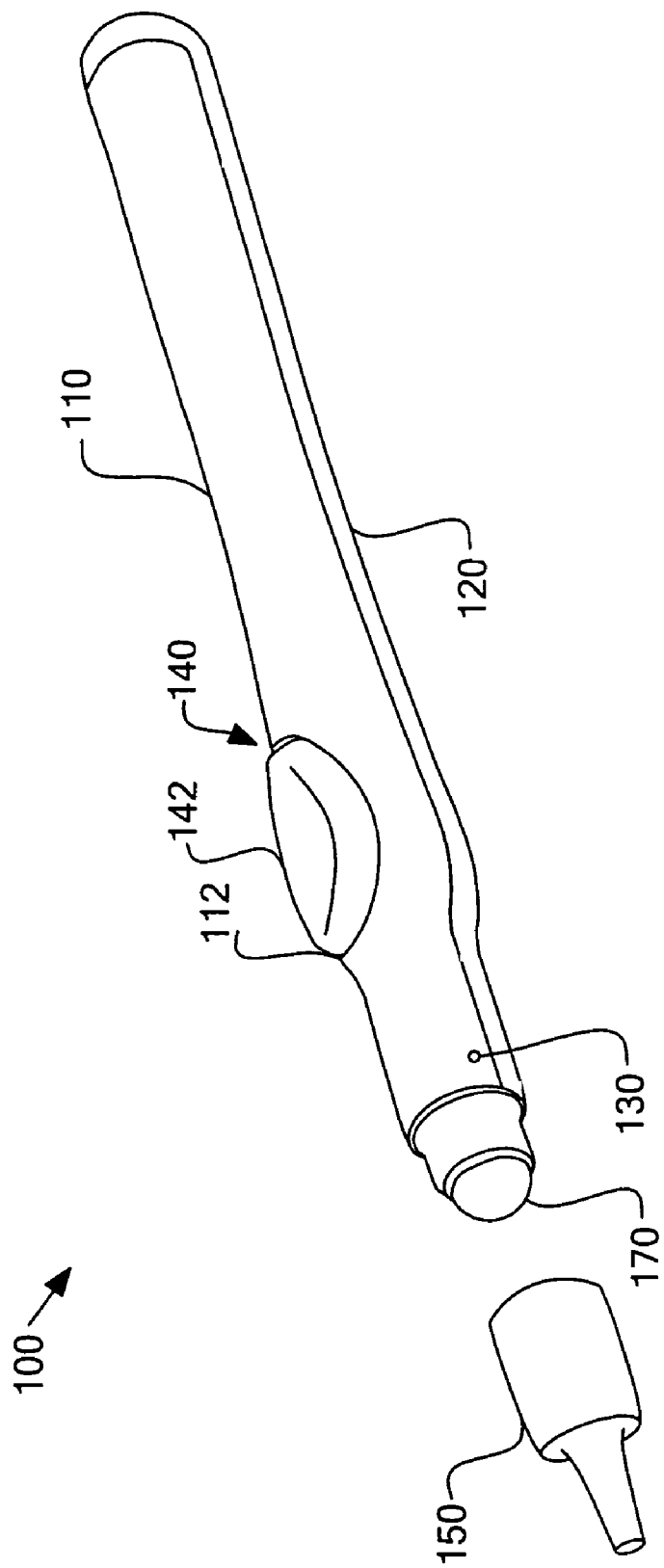
FIG. 2 is a perspective view of the exemplary embodiment of FIG. 1 illustrating activation of the applicator/dispenser.

FIGS. 1-4 illustrate a first embodiment of this invention, although this invention is in no way limited to the specific design depicted therein. As shown in FIGS. 1 and 2, an applicator/dispenser 100 is formed by a first body portion 110 and a second body portion 120 that are movable relative to one another. For example, in the embodiment shown, a pivoting connection 130 is provided that allows the first body portion 110 and the second body portion 120 to be moved from an open, spaced apart relative position, illustrated in FIG. 1, to a substantially closed, adjacent position, illustrated in FIG. 2. The relative position illustrated in FIG. 1 may be a "cocked" position in embodiments that have an amount of polymerizable adhesive material prepackaged in the applicator/dispenser 100.

The first body portion 110 and the second body portion 120 define a space therebetween into which a bladder 140 may be fitted. As shown in FIGS. 1 and 2, the first body portion 110 has an opening 112 through which a push button portion 142 of the bladder 140 may extend. As explained below, the push button portion 142 may be depressed by a user to dispense a desired quantity of polymerizable adhesive material from the applicator/dispenser 100, for example, through a detachable or replaceable tip 150. A user's thumb or finger may be used to depress the push button portion 142 while the applicator/dispenser 100 is held by the first and second body portions 110, 120 as a handle. For example, a user may hold the applicator/dispenser 100 as a pen and press the push button portion 142 with an index finger.

It should be understood that the detachable or replaceable tip 150 is optional and may have any desired configuration. If the detachable or replaceable tip 150 is not provided or used, a porous plug 170, described below, may form the tip of the dispenser/applicator 100. The tip 150 may be selected for a particular application, and is not limited to the tapered nozzle design shown. For example, the applicator tip may be a fibrous swab, a sponge swab, a foam swab, a brush, a spatula or the like. Any suitable tip, either known or hereafter developed, may be used with the applicators/dispensers according to this invention.

The tip 150 may be designed to friction fit over an end portion 160 of the applicator/dispenser 100. Alternatively, the tip 150 may fit directly on the porous plug 170 that is situated in an open end of the bladder 140, as described below.

The first body portion 110, the second body portion 120, the bladder 140 and/or the tip 150 may be made of any suitable material, preferably a material that promotes stability of the polymerizable adhesive material to be dispensed so as to avoid premature polymerization.

The porous plug 170 may include a polymerization initiator or rate modifier for the polymerizable adhesive material to be dispensed. The porous plug 170 may be impregnated with the polymerization initiator or rate modifier, or may have the polymerization initiator or rate modifier coated on a surface thereof.

Figure 3:
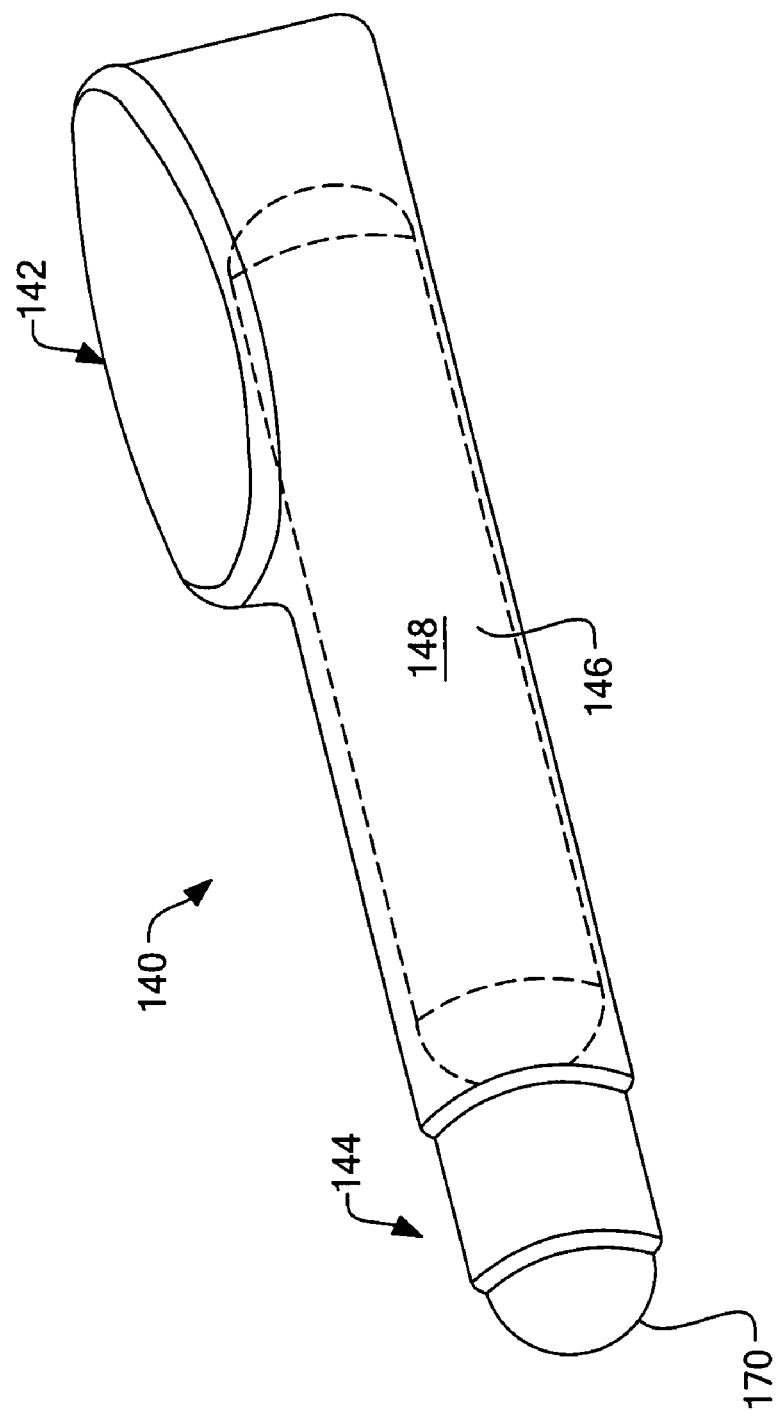
FIG. 3 is a perspective view of a bladder portion and an ampoule of the exemplary embodiment of FIG. 1.

FIG. 3 shows an exemplary embodiment of the bladder 140 removed from the applicator/dispenser 100. As described above, the bladder 140 has an open end 144 into which the porous plug 170 is fitted. At least the push button portion 142 of the bladder 140 is made of a flexible material. The bladder 140 may be blow molded of a suitable rubber, silicone or plastic material, such as, for example, polyvinyl chloride, polyethylene, polyurethane, natural or nitril rubber, or any combination thereof.

A frangible ampoule 146 containing an amount of polymerizable adhesive 148 is disposed in the bladder 140. The frangible ampoule 146 may be made of any suitable material, preferably a material that promotes stability and shelf-life of the polymerizable adhesive material 148. For example, the frangible ampoule 146 may be made of glass. Other materials, such as, a plastic material or pierceable metal, such as aluminum, may be used for the frangible ampoule 146. An example of a suitable ampoule that can be used in the dispenser/applicators of the present invention is disclosed in, for example, U.S. Pat. No. 5,928,611, the entire disclosure of which is incorporated herein by reference. In fact, where such an ampoule is used in the present invention, the entire ampoule/applicator device may be used, which would thereby constitute not only the ampoule 144, but also the porous plug 170. In such embodiments, the dispensers/applicators of the present invention are particularly suitable for dispensing or applying the adhesive contained in the DERMABOND® topical skin adhesive product, available from Ethicon (Somerville, N.J.).

Figure 4:
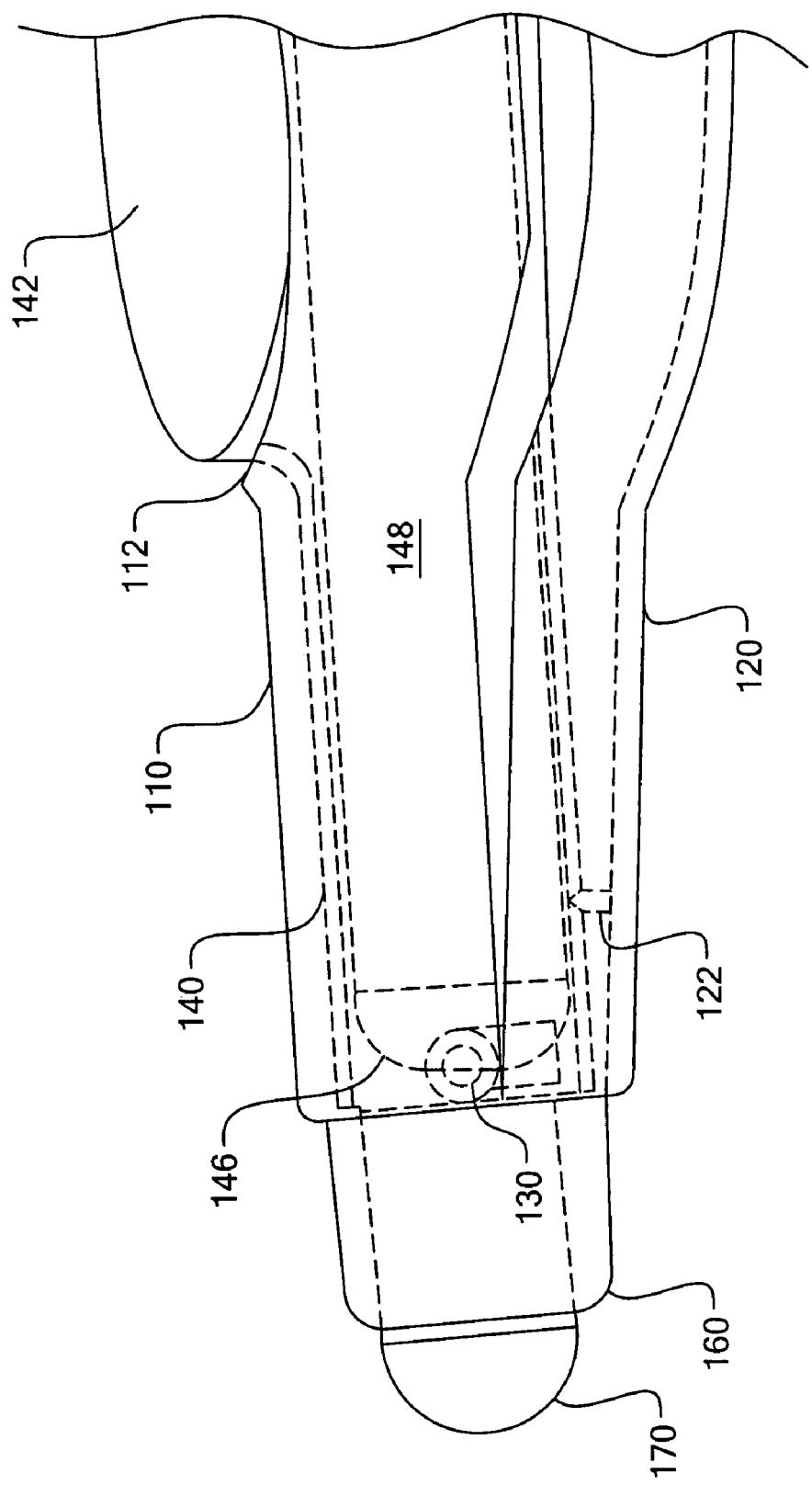
FIG. 4 is a partial cross-sectional view of the exemplary embodiment of FIG. 1.

FIG. 4 illustrates the bladder 140, the push button portion 142, the frangible ampoule 146 and the porous plug 170 assembled and inserted into the space between the first body portion 110 and the second body portion 120, with the porous plug 170 extending through an opening in the end portion 160 of the applicator/dispenser 100. As shown in FIG. 4, the second body portion 120 includes a piercing or breaking member 122 that extends inwardly from an inner surface thereof. The breaking member 122 is located so that the frangible ampoule 146 is broken by the breaking member 122 when the first and second body portions 110, 120 are moved from the open position shown in FIG. 1 to the closed position shown in FIG. 2. The first and second body portions 110, 120 act as levers on the pivoting connection 130, thus providing a mechanical advantage to facilitate breakage of the frangible ampoule 146.

Once the first and second body portions 110, 120 are moved to the closed position shown in FIG. 2 and the frangible ampoule 146 is broken, the first and second body portions 110, 120 may be prevented from accidentally returning to the open position shown in FIG. 1. For example, a detent or other suitable latching mechanism may be used to engage the first and second body portions 110, 120. In embodiments where the applicator/dispenser 100 is only to be used with the amount of polymerizable adhesive material 148 initially supplied, the latching mechanism may be irreversible.

In the embodiment shown, the breaking member 122 is situated remote from the push button portion 142 and near the open end 144 of the bladder 140. This location causes the frangible ampoule 146 to be broken near the open end 144 of the bladder 140 to help ensure that the polymerizable adhesive 148 will flow from the bladder 140 and that the flow is not impeded by larger fragments of the broken ampoule 146. Further, breaking the frangible ampoule 146 remote from the push button portion 142 may help to avoid fragments that could accidentally pierce the push button portion 142 and cut a user's thumb or finger. Although not shown, the bladder 140 may be thicker or reinforced at the push button 142 to prevent such an occurrence. Alternatively, the ampoule 146 may be placed within a separate tube-like structure, such as a standard butyrate tube, having a section removed, such as a partially opened end. Fragments of the broken ampoule 146 can be contained by the tube while allowing the polymerizable adhesive 148 to flow from the tube and from the bladder 140.

The bladder 140 is designed to contain the polymerizable adhesive 148 once the frangible ampoule 146 is broken. The polymerizable adhesive 148 may be forced from the bladder 140 by depressing the push button portion 142, displacing the polymerizable adhesive 148 and causing it to flow through the porous plug 170. The polymerizable adhesive 148 flowing through the porous plug 170 may be applied directly to a desired site using the porous plug 170 as an applicator tip. Alternatively, the detachable or replaceable tip 150 may receive the polymerizable adhesive 148 flowing through the porous plug 170 for application.

A controlled flow of the polymerizable adhesive 148 may be obtained by providing a slow, but steady pressure on the bladder 140, for example, by depressing the push button portion 142 to a desired extent and/or a desired number of times. In embodiments, the volume displaced by depressing the push button portion 142 may correspond to a desired amount of the polymerizable adhesive 148 that is to be dispensed.

As noted above, the amount of polymerizable adhesive material 148 may be prepackaged in the applicator/dispenser 100. The applicator/dispenser 100 may be disposable and discarded after the amount of polymerizable adhesive material 148 in the frangible ampoule 146 has been dispensed or otherwise been used (i.e., polymerized). Alternatively, the amount of polymerizable adhesive material 148 may be separate from the applicator/dispenser 100 and supplied to the applicator/dispenser 100 prior to use.

In embodiments, a user may be able to select from a variety of adhesive materials and/or amounts by selecting a frangible ampoule and/or bladder assembly (bladder, ampoule and plug) to be installed in the applicator/dispenser 100. For example, a kit may be provided that includes at least one applicator/dispenser 100 and a plurality of frangible ampoules 146 (or bladder assemblies). A plurality of detachable or replaceable tips 150 may also be included in the kit. The kit may also include a cleaning agent, such as isopropyl alcohol or other chemical sterilants, such as gluteraldehyde. Parts of the kit, such as the frangible ampoules 146 (or bladder assemblies) may be packaged separately, for example, in a blister pouch, and may be unpackaged and combined with the applicator/dispenser 100 as needed.

Figure 5:
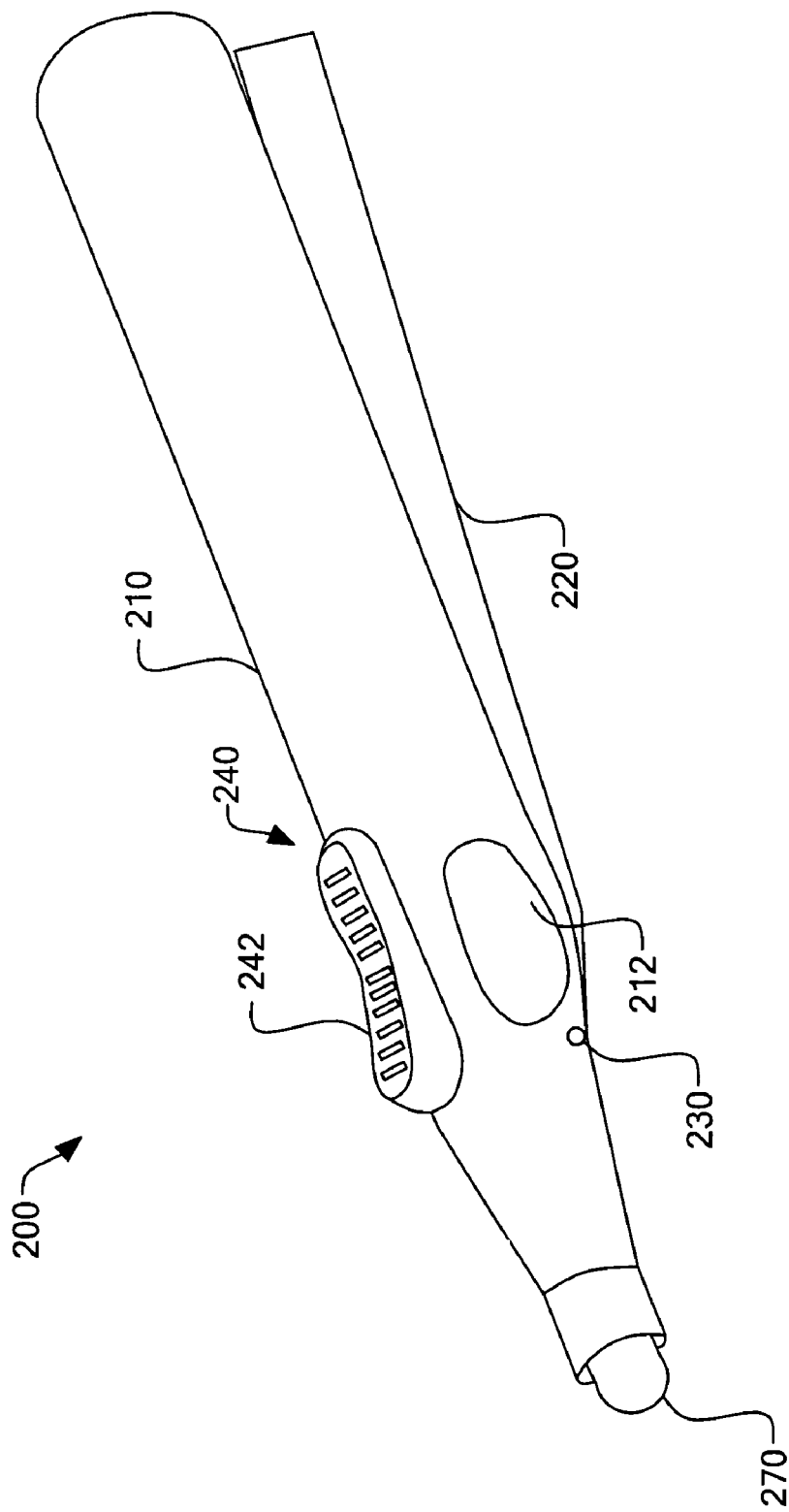
FIG. 5 is a perspective view of a second exemplary embodiment of this invention.
Figure 6:
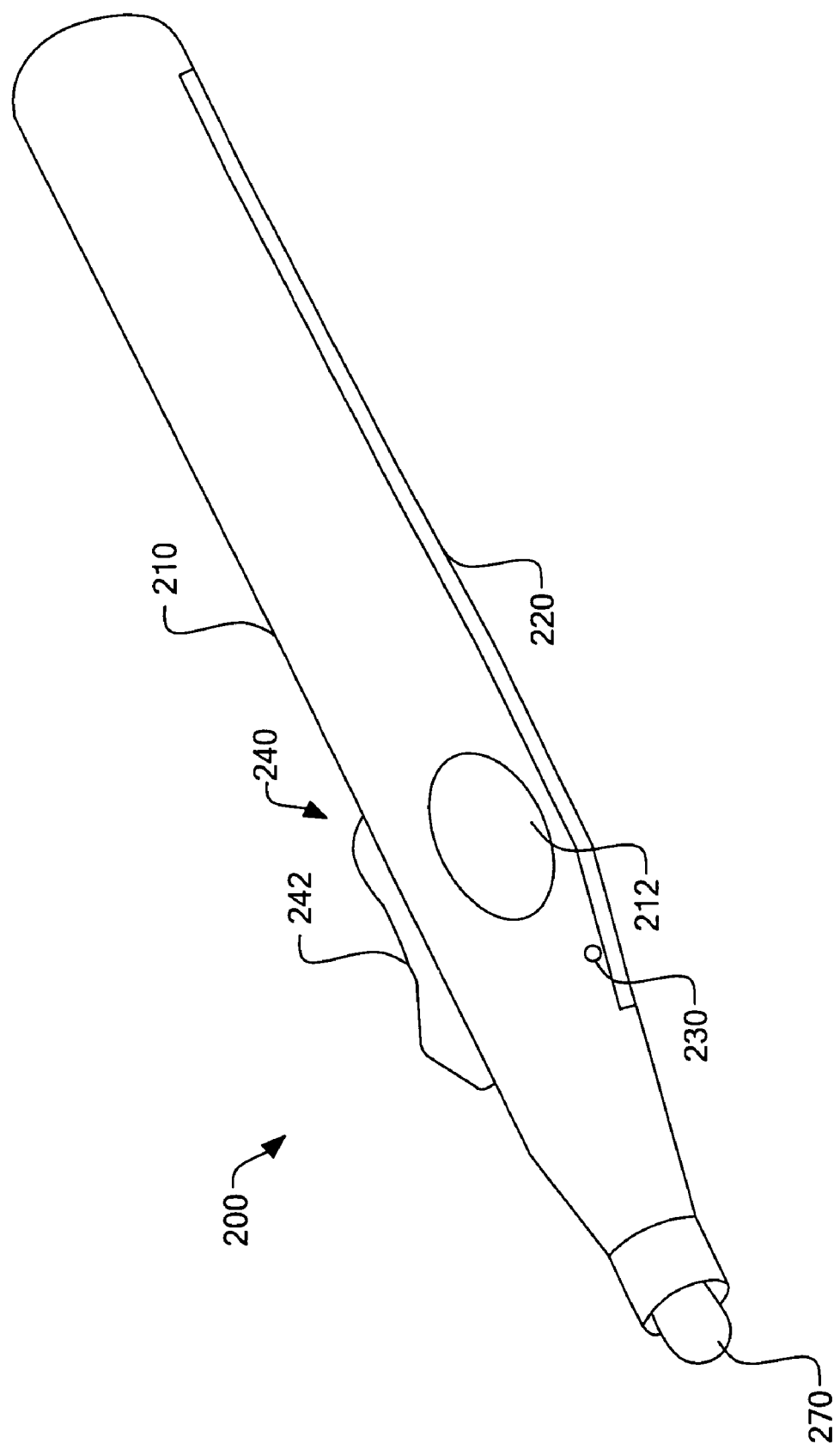
FIG. 6 is a perspective view of the exemplary embodiment of FIG. 5 illustrating activation of the applicator/dispenser.

FIGS. 5-9 illustrate a second embodiment of this invention, although this invention is in no way limited to the specific design depicted therein. As shown in FIGS. 5 and 6, an applicator/dispenser 200 is formed by a first body portion 210 and a second body portion 220 that are movable relative to one another. For example, in the embodiment shown, a pivoting connection 230 is provided that allows the first body portion 210 and the second body portion 220 to be moved from an open position, illustrated in FIG. 5, to a substantially closed position, illustrated in FIG. 6. The open position illustrated in FIG. 5 may be a "cocked" position in embodiments that have an amount of polymerizable adhesive material prepackaged in the applicator/dispenser 200.

As shown in FIGS. 5 and 6, the first body portion 210 has an opening through which a slide button portion 242 of a slider assembly 240 may extend. As explained below, the slide button portion 242 may be moved by a user to dispense a desired quantity of polymerizable adhesive material from the applicator/dispenser 200, for example, through a porous plug 270 or other suitable tip. A user's thumb or finger may be used to move the slide button 242 while the applicator/dispenser 200 is held by the first and second body portions 210, 220 as a handle. For example, a user may hold the applicator/dispenser 200 as a pen and push or slide forward the slide button 242 with an index finger. The first body portion 210 may include one or more contours 212 for a user's thumb or finger.

The slide button 242 is not limited to the specific embodiment shown FIGS. 5-9. The slide button 242 may be formed by a lever or other suitable mechanism, such as a syringe shaft, that is arranged to move the plunger portion 244 forward.

Figure 7:
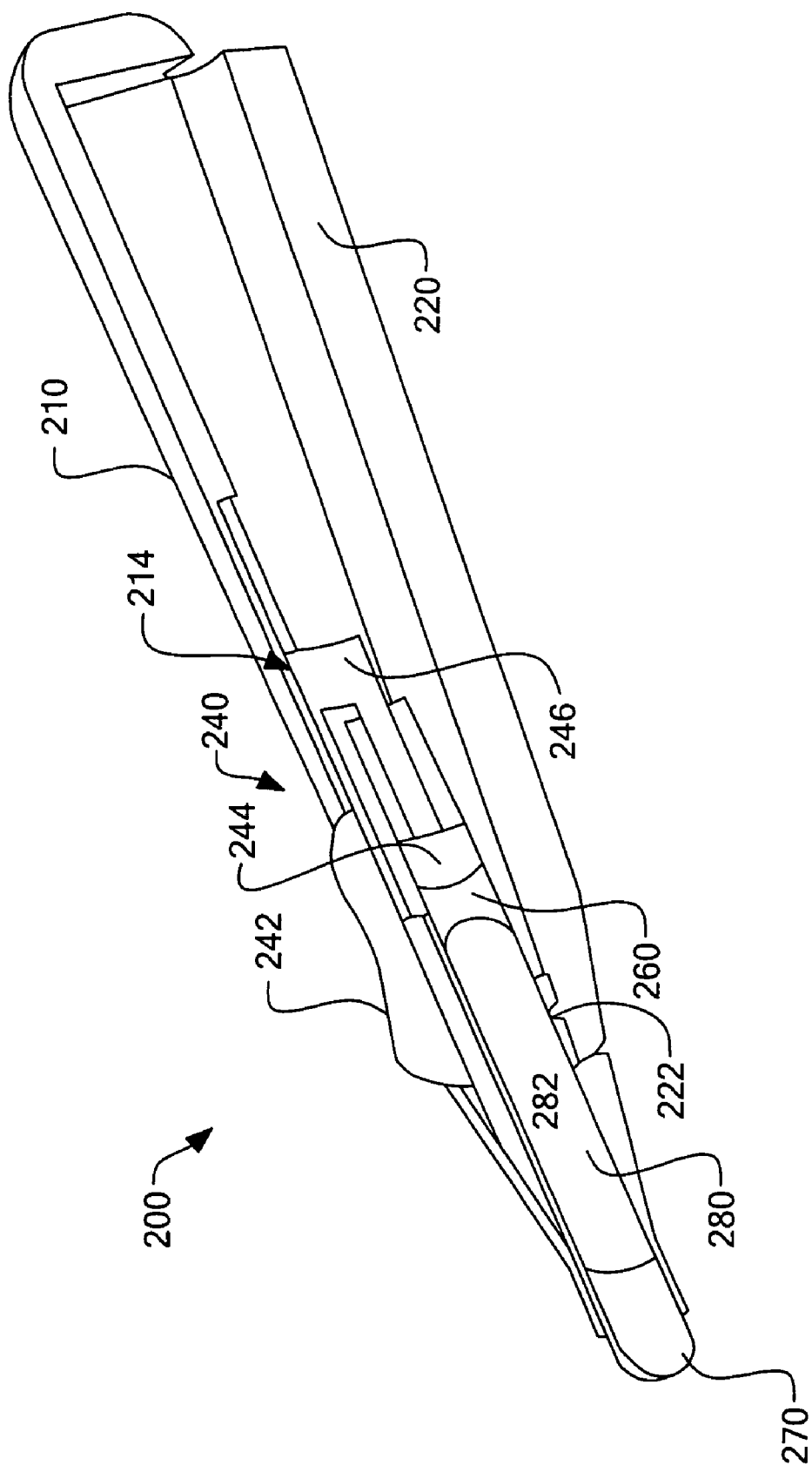
FIG. 7 is a cross-sectional view of the exemplary embodiment of FIG. 5.

FIG. 7 shows a cross-sectional view of the applicator/dispenser 200 with the first and second body portions 210, 220 in the open position. As shown, the first and second body portions 210, 220 define a chamber 260 into which a frangible ampoule 280 containing an amount of polymerizable adhesive material 282 may be placed. As shown in FIG. 7, the first body portion 210 has an opening 214 through which the slide button portion 242 of the slide assembly 240 may extend. In the embodiment shown, the opening 214 is an elongated slot that allows the slide assembly to move in an axial direction of the applicator/dispenser 200. Thus, as explained below, the slide button portion 242 may be moved by a user to move a plunger portion 244 of the slide assembly 240. Once the frangible ampoule 280 is broken by a piercing or breaking member 222 provided, for example, on the second body portion 220, movement of the plunger portion 244 toward the porous plug 270 will cause the polymerizable adhesive material 282 to be dispensed from the applicator/dispenser 200.

Although not shown, it should be understood that the second embodiment may also include a detachable or replaceable tip as described above with respect to the first embodiment.

Figure 8:
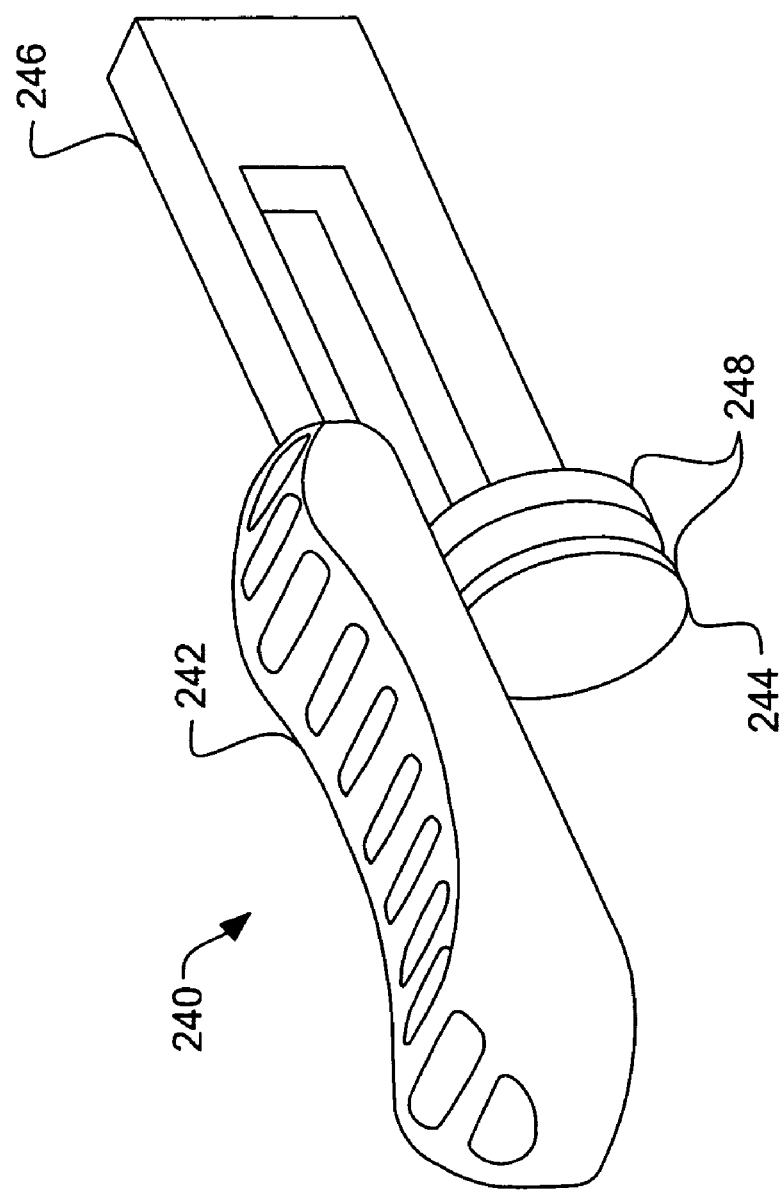
FIG. 8 is a perspective view of a slider assembly of the exemplary embodiment of FIG. 5.

FIG. 8 shows an exemplary embodiment of the slide assembly 240 removed from the applicator/dispenser 200.

The slide button portion 242 and the plunger portion 244 are connected by an intermediate portion 246 of the slide assembly 240. The intermediate portion 246 should be sufficiently rigid to carry the plunger portion 244 against any resistance caused by the polymerizable adhesive material 282, contact between the plunger portion 244 and the chamber 260, and/or the broken ampoule 280. On the other hand, the slide button portion 242 may be made of a rubber material or a plastic material that is comfortable and/or provides a suitable grip for a user's finger or thumb. The plunger portion 244 may be made of a rubber material or a plastic material that will slide within the chamber 260 while providing a sufficient seal against the inner surface of the chamber 260 to prevent substantial leakage of the polymerizable adhesive material 282 during use. Alternatively, the plunger portion 244 may be provided with one or more seal rings 248 of a suitable material. The slide button portion 242 and the intermediate portion 246 may be made of any variety of thermoplastics, such as ABS, polycarbonate, ULTEM™ and the like. The plunger portion 244 and/or the seal rings 248 may be made of any variety of rubbers, such as natural, nitril, polyisoprene and the like. A suitable lubricant may be provided to allow the plunger portion 244 and/or the seal rings 248 to slide while maintaining contact with the inside surface of the chamber 260. Preferably, the lubricant and the materials selected do not react with or cause premature polymerization of the adhesive material.

Figure 9:
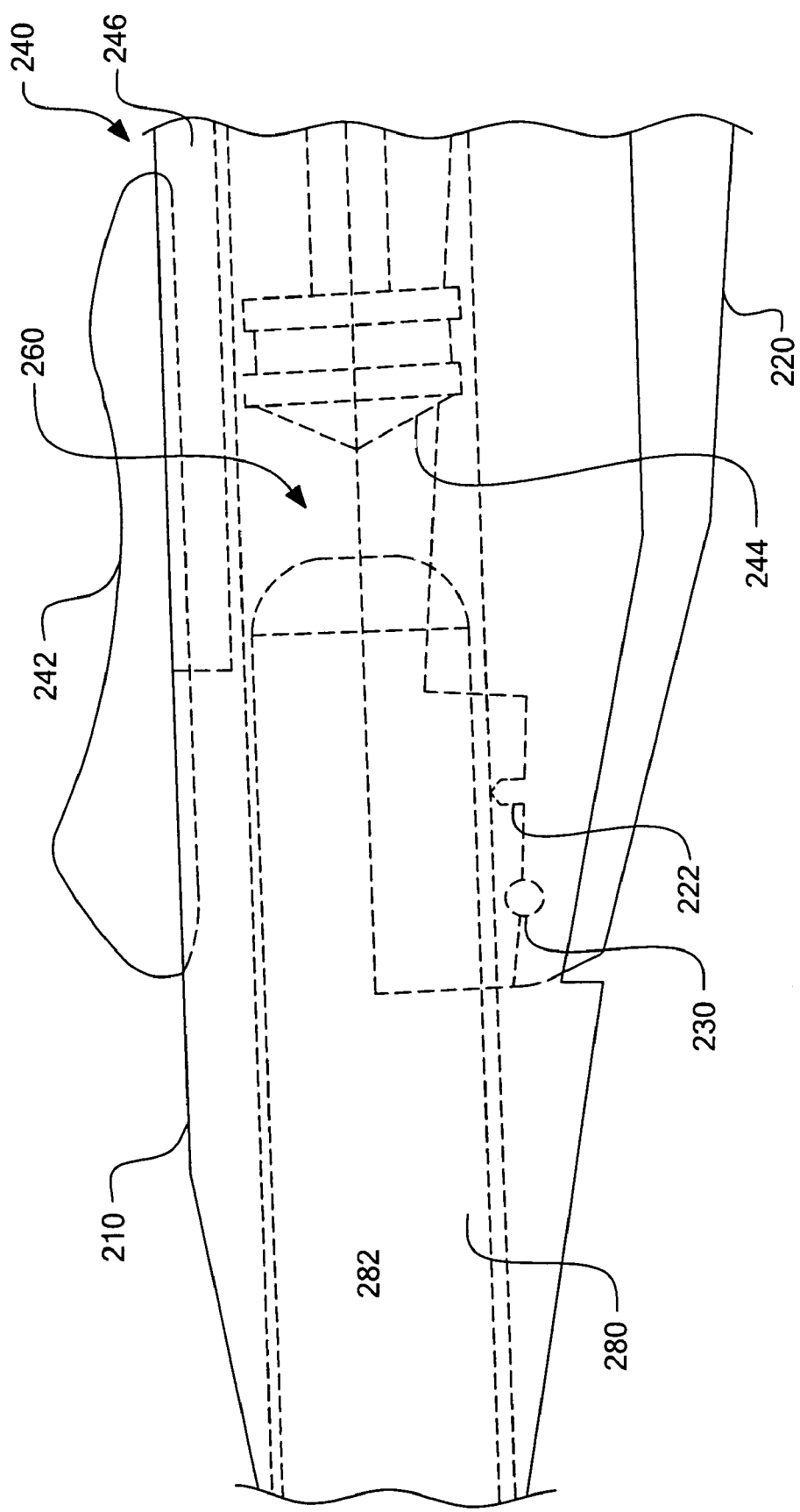
FIG. 9 is a partial cross-sectional view of the exemplary embodiment of FIG. 5.

FIG. 9 illustrates the slide assembly 240, the slide button 242, the plunger portion 244 and the frangible ampoule 280 inserted into the chamber 260. As shown in FIG. 9, the piercing or breaking member 222 extends inwardly from an inner surface of the second body portion 220. The breaking member 222 is located so that the frangible ampoule 280 is broken by the breaking member 222 when the first and second body portions 210, 220 are moved from the open position shown in FIG. 5 to the closed position shown in FIG. 6. The first and second body portions 210, 220 act as levers on the pivoting connection 230, thus providing a mechanical advantage to facilitate breakage of the frangible ampoule 280.

As described above with respect to the first embodiment, once the first and second body portions 210, 220 are moved to the closed position shown in FIG. 6 and the frangible ampoule 280 is broken, the first and second body portions 210, 220 may be prevented from accidentally returning to the open position shown in FIG. 5.

Although the breaking member 222 is situated near an end of the frangible ampoule 280 remote from the porous plug 270 in the embodiment shown, the breaking member 222 and frangible ampoule may be located so that the frangible ampoule 280 will be broken near an end closer to the porous plug 270 to help ensure that the polymerizable adhesive 282 will not impeded by larger fragments of the broken ampoule 280. Further, while the breaking member 222 is shown as single localized member, it should be understood that the breaking member 222 may extend along a portion of or the entire ampoule 280 and/or may comprise a plurality of breaking members. Further, while the ampoule 280 is shown as a single ampoule, it should be understood that a plurality of ampoules may be provided. For example, one ampoule may contain the adhesive material while another ampoule contains a bioactive material, such as a medicament, or other material.

The chamber 260 is designed to contain the polymerizable adhesive 282 once the frangible ampoule 280 is broken. The polymerizable adhesive 282 may be forced from the chamber 260 by moving the slide button portion 242 so that the plunger portion 244 of the slide assembly 240 displaces the polymerizable adhesive 282 and causes it to flow through the porous plug 270. The polymerizable adhesive 282 flowing through the porous plug 270 may be applied directly to a desired site using the porous plug 270 as an applicator tip. Alternatively, a detachable or replaceable tip may receive the polymerizable adhesive 282 flowing through the porous plug 270 for application.

A controlled flow of the polymerizable adhesive 282 may be obtained by moving the slide button portion 242 to a desired extent. In embodiments, movement of the slide assembly 240 may create a pressure within the dispenser/applicator 200 to force the polymerizable adhesive 282 to flow.

As noted above, the amount of polymerizable adhesive material 282 may be prepackaged in the applicator/dispenser 200. The applicator/dispenser 200 may be disposable and discarded after the amount of polymerizable adhesive material 282 in the frangible ampoule 280 has been dispensed or otherwise been used (i.e., polymerized). Alternatively, the amount of polymerizable adhesive material 282 may be separate from the applicator/dispenser 200 and supplied to the applicator/dispenser 200 prior to use.

In embodiments, a user may be able to select from a variety of adhesive materials and/or amounts by selecting a frangible ampoule to be installed in the applicator/dispenser 200. For example, a kit may be provided that includes at least one applicator/dispenser 200 and a plurality of frangible ampoules 280. A plurality of detachable or replaceable tips may also be included in the kit.

Figure 10:
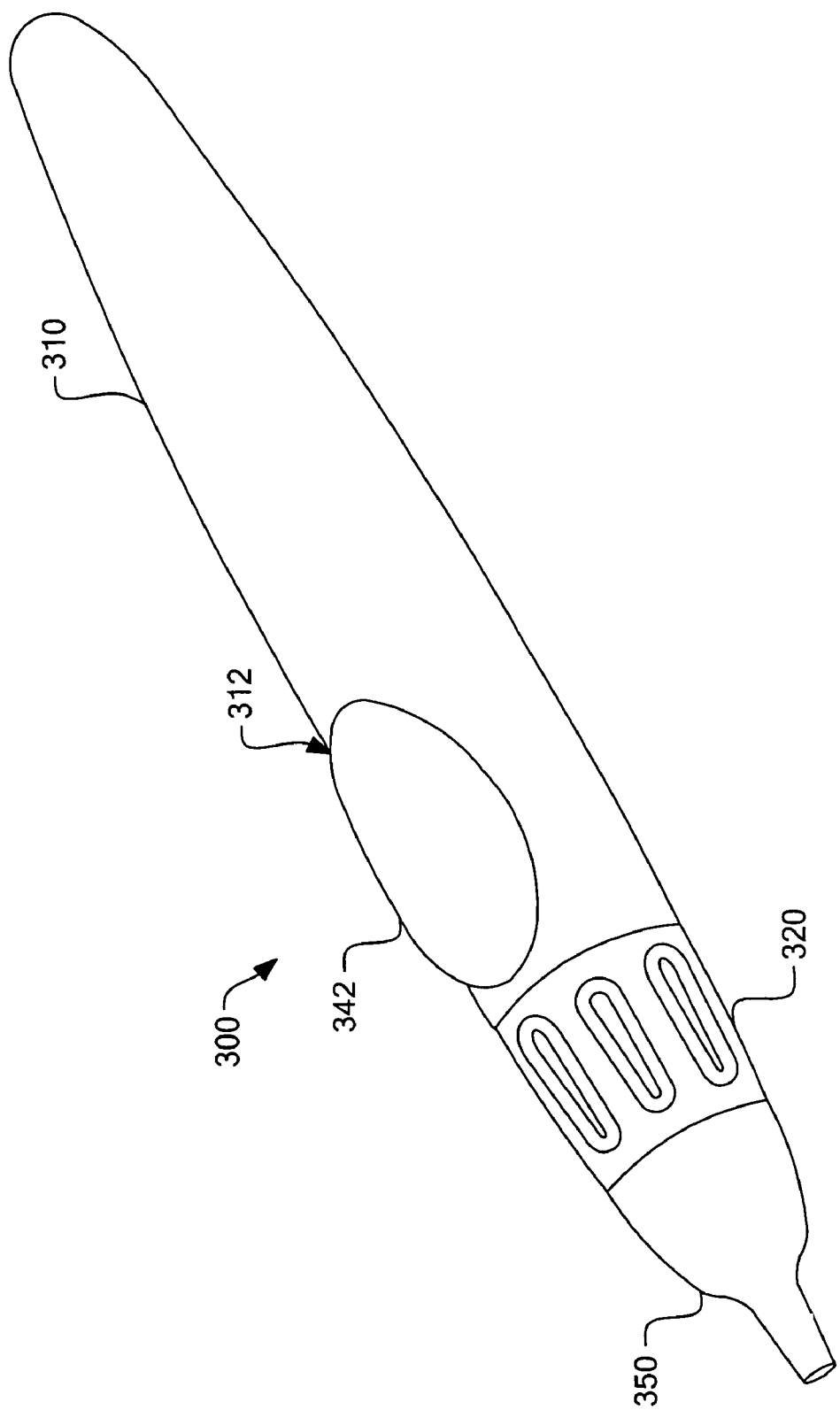
FIG. 10 is a perspective view of a third exemplary embodiment of this invention.
Figure 11:
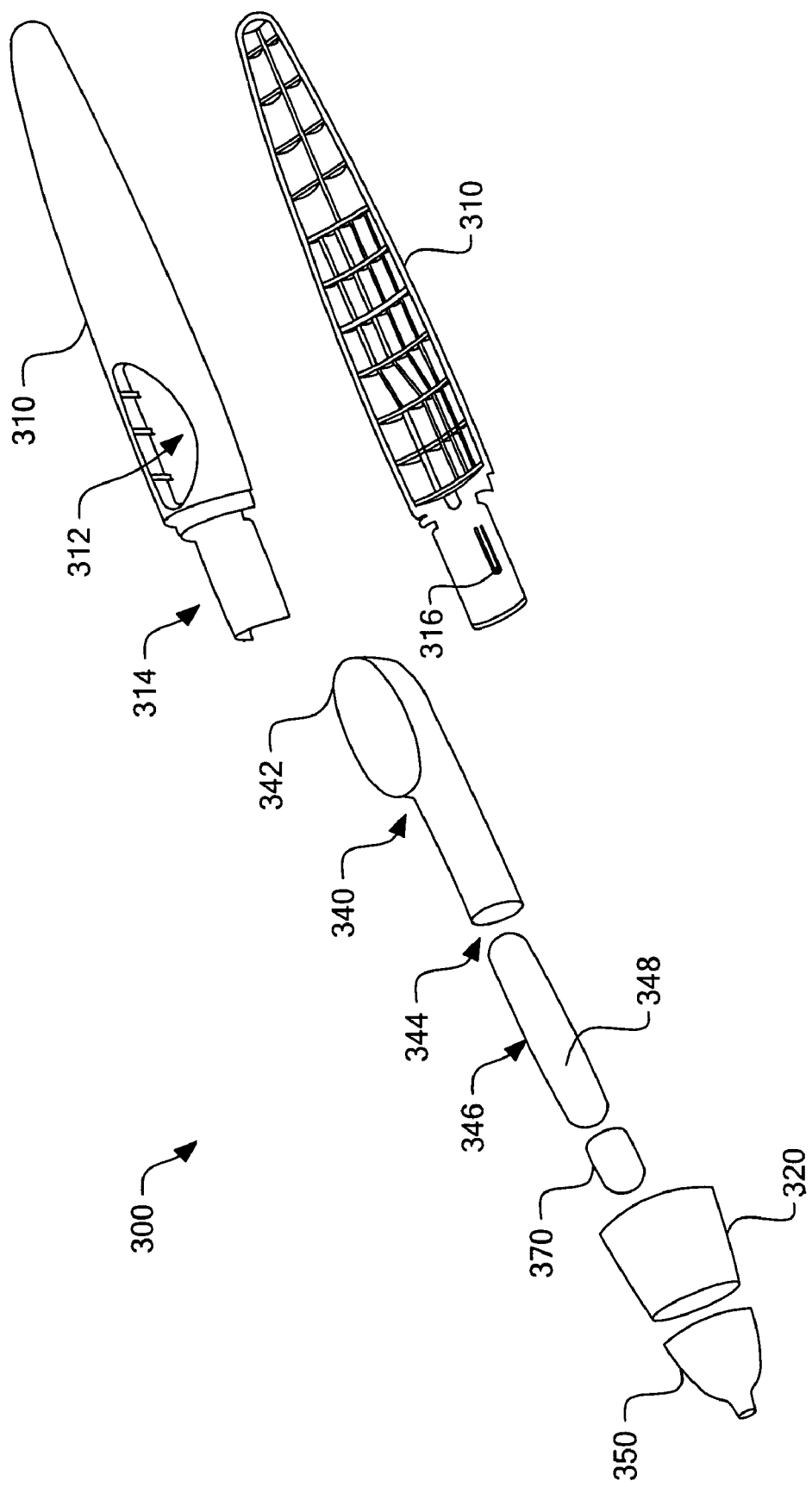
FIG. 11 is an exploded view of the exemplary embodiment of FIG. 10.
Figure 12:
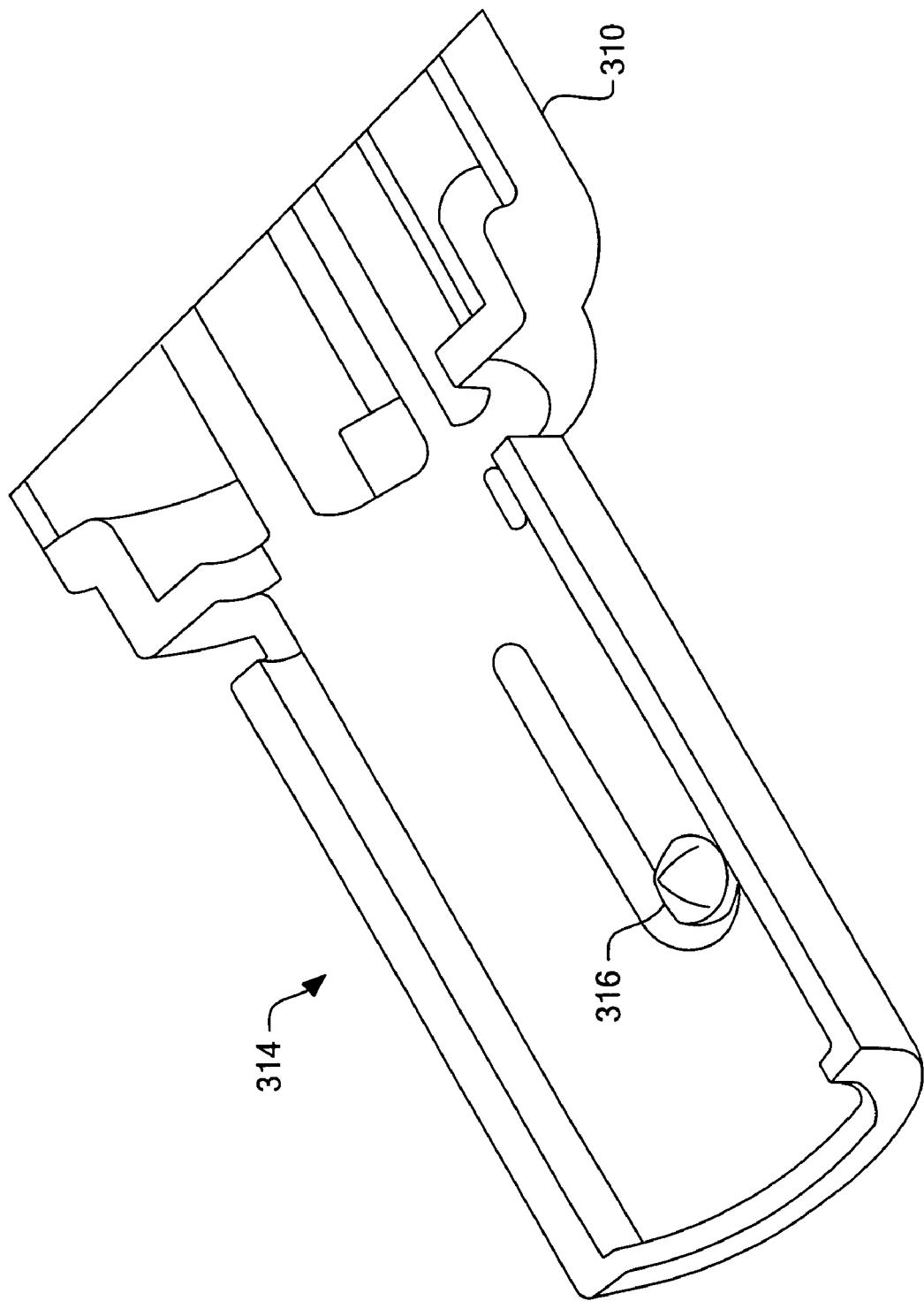
FIG. 12 is an enlarged, partial view of the exemplary embodiment of FIG. 10.

FIGS. 10-12 illustrate a third embodiment of this invention, although this invention is in no way limited to the specific design depicted therein. As shown in FIGS. 10 and 11, an applicator/dispenser 300 is formed by a first body portion 310 and a second body portion 320 that are movable relative to one another. For example, in the embodiment shown, the first body portion 310 may be formed by two pieces that fit together to provide an open end 314, as shown in FIG. 11. The second body portion 320 is rotatably situated on the end 314 of the first body portion 310.

As shown in FIGS. 10 and 11, the first body portion 310 has an opening 312 through which a push button portion 342 of the bladder 340 may extend. As explained below, the push button portion 342 may be depressed by a user to dispense a desired quantity of polymerizable adhesive material from the applicator/dispenser 300, for example, through a detachable or replaceable tip 350. A user's thumb or finger may be used to depress the push button portion 342 while the applicator/dispenser 300 is held by the first body portion 310 as a handle. For example, a user may hold the applicator/dispenser 300 as a pen and press the push button portion 342 with an index finger.

It should be understood that the detachable or replaceable tip 350 may have any desired configuration. The tip 350 may be selected for a particular application, and is not limited to the tapered nozzle design shown. For example, the applicator tip may be a fibrous swab, a sponge swab, a foam swab, a brush, a spatula or the like. Any suitable tip, either known or hereafter developed, may be used with the applicators/dispensers according to this invention.

The tip 350 may be designed to friction fit with the end 314 of the first body portion 310 of the applicator/dispenser 300. Alternatively, the tip 350 may fit directly on a porous plug 370 that is situated in an open end of the bladder 340, as described below. Further, the tip 350 may be nondetachable once the applicator/dispenser 300 has been assembled, for example, by connecting to the end 314 of the first body portion 310.

The first body portion 310, the second body portion 320, the bladder 340 and/or the tip 350 may be made of any suitable material, preferably a material that promotes stability of the polymerizable adhesive material to be dispensed so as to avoid premature polymerization.

The porous plug 370 may include a polymerization initiator or rate modifier for the polymerizable adhesive material to be dispensed. The porous plug 370 may be impregnated with the polymerization initiator or rate modifier, or may have the polymerization initiator or rate modifier coated on a surface thereof.

FIG. 11 shows an exploded view of the third exemplary embodiment. As described above with respect to the first embodiment, the bladder 340 has an open end 344 into which the porous plug 370 is fitted. At least the push button portion 342 of the bladder 340 is made of a flexible material. The bladder 340 may be blow molded of a suitable rubber or plastic material, such as, for example, polyvinyl chloride, polyethylene, polyurethane, natural rubber, nitril rubber, and the like.

A frangible ampoule 346 containing an amount of polymerizable adhesive 348 is disposed in the bladder 340. The frangible ampoule 346 may be made of any suitable material, preferably a material that promotes stability and shelf-life of the polymerizable adhesive material 348. For example, the frangible ampoule 346 may be made of glass. Other materials, such as, a plastic material or a pierceable metal material, such as aluminum, may be used for the frangible ampoule 346. Similar to the embodiment of FIGS. 1-4, discussed above, an example of a suitable ampoule that can be used in the dispenser/applicators of the present invention is disclosed in, for example, U.S. Pat. No. 5,928,611, the entire disclosure of which is incorporated herein by reference. In fact, where such an ampoule is used in the present invention, the entire ampoule/applicator device may be used, which would thereby constitute not only the ampoule 346, but also the porous plug 370. In such embodiments, the dispensers/applicators of the present invention are particularly suitable for dispensing or applying the adhesive contained in the DERMABOND® topical skin adhesive product, available from Ethicon (Somerville, N.J.).

The bladder 340, the push button portion 342, the frangible ampoule 346 and the porous plug 370 may be assembled and inserted into the space between the two pieces of the first body portion 310, with the porous plug 370 extending through the open end 314 of the first body portion 310 and the second body portion 320 rotatably situated on the end 314 of the first body portion 310.

As shown in FIGS. 11 and 12, the end 314 of the first body portion 310 includes a piercing or breaking member 316 that extends inwardly. The breaking member 316 is located so that the frangible ampoule 346 is broken by the breaking member 316 when the first and second body portions 310, 320 are rotated relative to one another so that a camming surface or inclined ramp located on an inner surface of the second body portion 320 presses the breaking member 316 into the frangible ampoule 346. Upon relative rotation, the camming surface or ramp contacts a portion of the breaking member 316 that extends beyond the outer surface of the end 314 and presses the breaking member 316 inwardly against the frangible ampoule 346. The camming surface or ramp provides a mechanical advantage to facilitate breakage of the frangible ampoule 346.

The bladder 340 is designed to contain the polymerizable adhesive 348 once the frangible ampoule 346 is broken. The polymerizable adhesive 348 may be forced from the bladder 340 by depressing the push button portion 342, displacing the polymerizable adhesive 348 and causing it to flow through the porous plug 370. The polymerizable adhesive 348 flowing through the porous plug 370 may be applied to a desired site using the tip 350.

A controlled flow of the polymerizable adhesive 348 may be obtained by depressing the push button portion 342 to a desired extent and/or a desired number of times. In embodiments, the volume displaced by depressing the push button portion 342 may correspond to a desired metered amount of the polymerizable adhesive 348 that is to be dispensed.

As noted above, the amount of polymerizable adhesive material 348 may be prepackaged in the applicator/dispenser 300. The applicator/dispenser 300 may be disposable and discarded after the amount of polymerizable adhesive material 348 in the frangible ampoule 346 has been dispensed or otherwise been used (i.e., polymerized). Alternatively, the amount of polymerizable adhesive material 348 may be separate from the applicator/dispenser 300 and supplied to the applicator/dispenser 300 prior to use.

In embodiments, a user may be able to select from a variety of adhesive materials and/or amounts by selecting a frangible ampoule and/or bladder assembly (bladder, ampoule and plug) to be installed in the applicator/dispenser 300. For example, a kit may be provided that includes at least one applicator/dispenser 300 and a plurality of frangible ampoules 346 (or bladder assemblies). A plurality of detachable or replaceable tips 350 may also be included in the kit.

Figure 13:
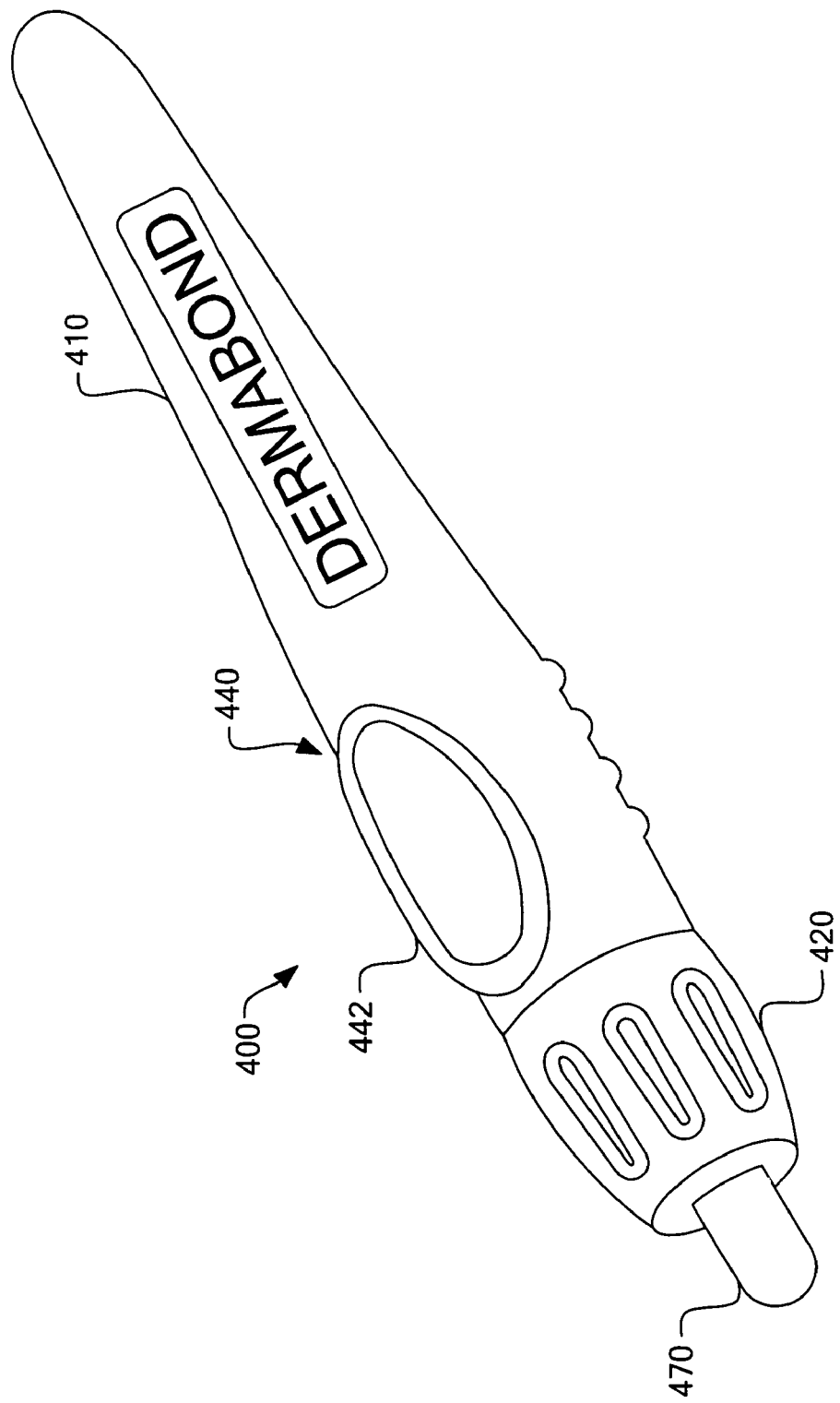
FIG. 13 is a top perspective view of a fourth exemplary embodiment of this invention.
Figure 14:
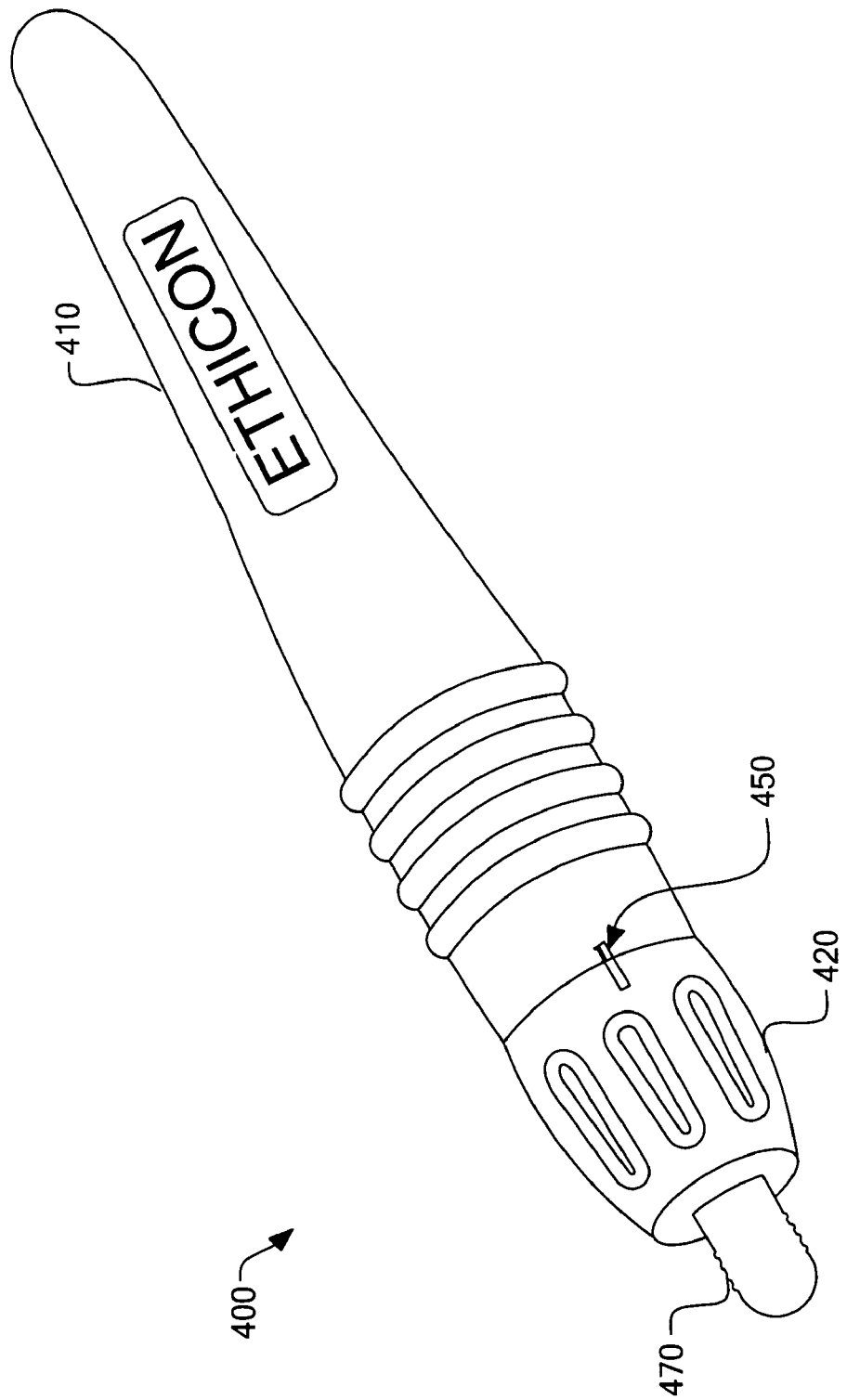
FIG. 14 is a bottom perspective view of the exemplary embodiment of FIG. 13.
Figure 15:
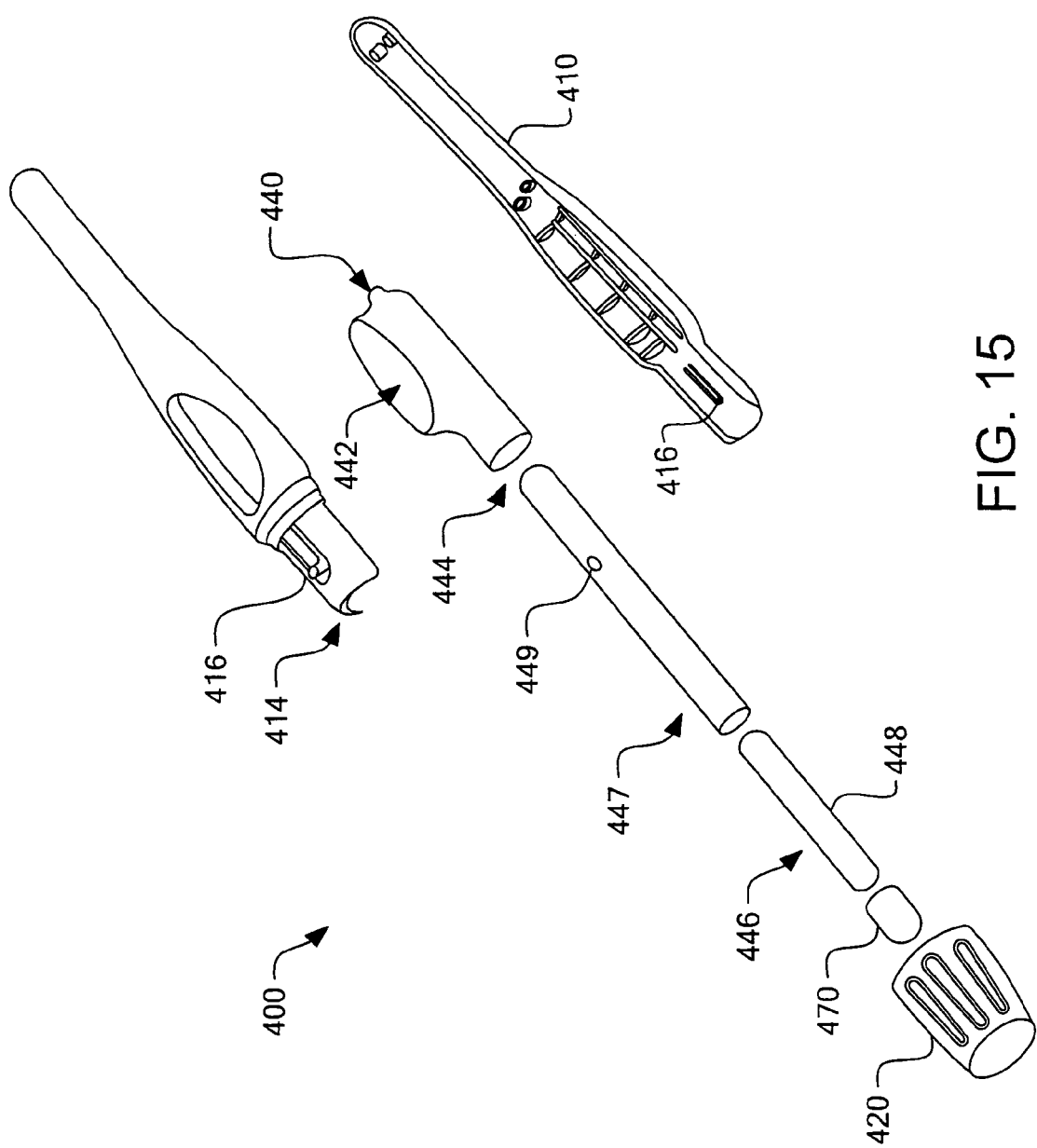
FIG. 15 is an exploded view of the exemplary embodiment of FIG. 13.

FIGS. 13-15 illustrate a fourth embodiment of this invention, although this invention is in no way limited to the specific design depicted therein. As shown in FIGS. 13-15, an applicator/dispenser 400 is formed by a first body portion 410 and a second body portion 420 that are movable relative to one another. For example, in the embodiment shown, the first body portion 410 may be formed by two pieces that fit together to provide an open end 414, as shown in FIG. 15. The second body portion 420 is rotatably situated on the end 414 of the first body portion 410.

As shown in FIGS. 13-15, the first body portion 410 has an opening 412 through which a push button portion 442 of the bladder 440 may extend. As explained below, the push button portion 442 may be depressed by a user to dispense a desired quantity of polymerizable adhesive material from the applicator/dispenser 400, for example, through a detachable or replaceable tip (not shown). A user's thumb or finger may be used to depress the push button portion 442 while the applicator/dispenser 400 is held by the first body portion 410 as a handle. For example, a user may hold the applicator/dispenser 400 as a pen and press the push button portion 442 with an index finger.

The first body portion 410, the second body portion 420, and/or the bladder 440 may be made of any suitable material, preferably a material that promotes stability of the polymerizable adhesive material to be dispensed so as to avoid premature polymerization.

A porous plug 470 is situated in an open end of the bladder 440, as further described below. The porous plug 470 may include a polymerization initiator or rate modifier for the polymerizable adhesive material to be dispensed. The porous plug 470 may be impregnated with the polymerization initiator or rate modifier, or may have the polymerization initiator or rate modifier coated on a surface thereof.

FIG. 15 shows an exploded view of the fourth exemplary embodiment. As described above with respect to the first embodiment, the bladder 440 has an open end 444 into which the porous plug 470 is fitted. At least the push button portion 442 of the bladder 440 is made of a flexible material. The bladder 440 may be blow molded of a suitable rubber or plastic material, such as, for example, polyvinyl chloride, polyethylene, polyurethane, natural rubber, nitril rubber, and the like.

A frangible ampoule 446 containing an amount of polymerizable adhesive 448 is disposed in the bladder 440. The frangible ampoule 446 may be made of any suitable material, preferably a material that promotes stability and shelf-life of the polymerizable adhesive material 448. For example, the frangible ampoule 446 may be made of glass. Other materials, such as, a plastic material or a pierceable metal material, such as aluminum, may be used for the frangible ampoule 446. Similar to the embodiment of FIGS. 1-4, discussed above, an example of a suitable ampoule that can be used in the dispenser/applicators of the present invention is disclosed in, for example, U.S. Pat. No. 5,928,611, the entire disclosure of which is incorporated herein by reference. In fact, where such an ampoule is used in the present invention, the entire ampoule/applicator device may be used, which would thereby constitute not only the ampoule 446, but also the porous plug 470. In such embodiments, the dispensers/applicators of the present invention are particularly suitable for dispensing or applying the adhesive contained in the DERMABOND® topical skin adhesive product, available from Ethicon (Somerville, N.J.).

In the fourth embodiment, the ampoule 446 is surrounded by a tube 447. The tube 447 may be of any suitable material that is compatible with the particular adhesive to be applied, such as, for example, buterate or polyethylene, and may be selected based on a desired application.

As shown, the tube 447 has a hole 449 formed therein. When assembled, the tube 447 is positioned in the bladder 440 so that the hole 449 is placed in communication with the interior of the push button portion 442 of the bladder 440. As described below, this allows the depression of the push button 442 to apply pressure to expel the adhesive 448. In embodiments, the tube 447 is fixed or bonded to the bladder 440 so that the hole 449 is maintained in a proper position.

The bladder 440, the push button portion 442, the frangible ampoule 446, the tube 447 and the porous plug 470 may be assembled and inserted into the space between the two pieces of the first body portion 410, with the porous plug 470 extending through the open end 414 of the first body portion 410 and the second body portion 420 rotatably situated on the end 414 of the first body portion 410.

Figure 16:
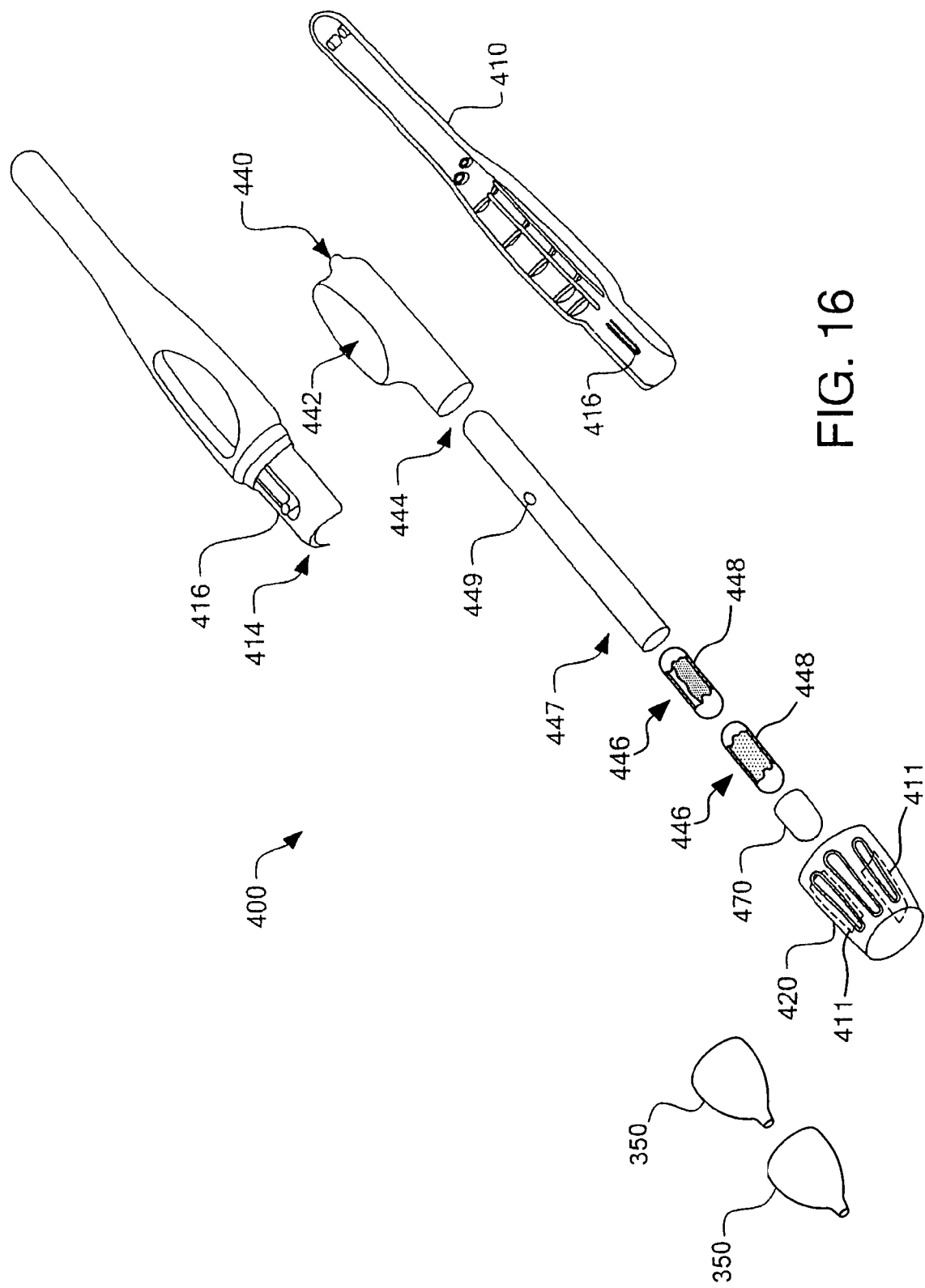
FIG. 16 is another embodiment of FIG. 15.

As shown in FIG. 15 and FIG. 16, and as described above with respect to FIGS. 11 and 12 of the third embodiment, the end 414 of the first body portion 410 includes a piercing or breaking member 416 that extends inwardly. In the fourth embodiment, two breaking members 416 are provided that may be positioned opposite each other. The breaking members 416 are located so that the frangible ampoule 446 is broken by the breaking members 416 when the first and second body portions 410, 420 are rotated relative to one another so that corresponding camming surfaces or inclined ramps 411 located on an inner surface of the second body portion 420 press the breaking members 416 into the frangible ampoule 446. Upon relative rotation, the camming surfaces or ramps contact a portion of the corresponding breaking members 416 that extend beyond the outer surface of the end 414 and press the breaking members 416 inwardly against the tube 447 to apply pressure on the frangible ampoule 446. The camming surfaces or ramps provide a mechanical advantage to facilitate breakage of the frangible ampoule 446. Further, because the breaking members 416 are positioned opposite each other, the frangible ampoule 446 is held in place to facilitate breakage.

As shown in FIG. 14, the applicator/dispenser 400 has a visual indicator 450 that allows a user to determine whether the applicator/dispenser 400 has been activated. The visual indicator 450 may be a set of raised features, as shown, or any other suitable set of markings, that allow a user to identify when the first and second body portions, 410, 420 are rotated relative to each other. For example, the visual indicator 450 may be initially aligned prior to activation of the applicator/dispenser 400, as shown in FIG. 14. Relative rotation of the first and second body portions, 410, 420 is thus clearly indicated by the visual indicator 450 no longer being aligned.

Alternatively or additionally, the visual indicator 450 may comprise a second feature/marking or set of features/markings that indicate when the first and second body portions, 410, 420 are relatively rotated to a position in which the ampoule 446 is broken by the breaking members 416.

In the fourth embodiment, the tube or second container 447 is designed to contain the polymerizable adhesive 448 once the frangible ampoule 446 is broken. The polymerizable adhesive 448 may be forced from the tube 447 by depressing the push button portion 442 of the bladder 440, applying pressure via the hole 449, displacing the polymerizable adhesive 448 and causing it to flow through the porous plug 470. The polymerizable adhesive 448 flowing through the porous plug 470 may then be applied to a desired site.

A controlled flow of the polymerizable adhesive 448 may be obtained by depressing the push button portion 442 to a desired extent and/or a desired number of times. In embodiments, the volume displaced by depressing the push button portion 442 may correspond to a desired metered amount of the polymerizable adhesive 448 that is to be dispensed.

As noted above, the amount of polymerizable adhesive material 448 may be prepackaged in the applicator/dispenser 400. The applicator/dispenser 400 may be disposable and discarded after the amount of polymerizable adhesive material 448 in the frangible ampoule 446 has been dispensed or otherwise been used (i.e., polymerized). Alternatively, the amount of polymerizable adhesive material 448 may be separate from the applicator/dispenser 400 and supplied to the applicator/dispenser 400 prior to use.

In embodiments, a user may be able to select from a variety of adhesive materials and/or amount by selecting a frangible ampoule, a tube and/or bladder assembly (bladder, ampoule, tube and plug) to be installed in the applicator/dispenser 400. For example, a kit may be provided that includes at least one applicator/dispenser 400 and a plurality of containers of adhesive material, such as frangible ampoules 446 (or bladder assemblies) as shown in FIG. 16.

By making portions of the applicators/dispensers of this invention of a material that tends to stabilize the adhesive monomer composition, it is possible and preferred in embodiments of this invention that the adhesive composition does not include, or is substantially free of, one or more stabilizer components such as are known and used in the art as additives to the adhesive monomer composition. This may reduce, or even eliminate, the need for a polymerization initiator or accelerator. For example, suitable materials include those disclosed in copending U.S. patent application Ser. No. 09/874,039, filed Jun. 6, 2001, which is hereby incorporated herein by reference in its entirety. For example, suitable materials may include halogenated and/or fluorinated materials.

Suitable applicator tips, either the replaceable tip or the porous plug as described above, for the applicators/dispensers of this invention include swabs, brushes, spatulas, droppers, syringes, and the like. Any suitable applicator tip can be used that allows for application of the adhesive composition to the desired site, and thus different applicator tips may be appropriate for different application methods. The applicator tip can have a variety of suitable shapes, including, but not limited to, conical, cylindrical, chisel or polygonal shapes such as rectangular or trapezoidal. The length and size of the tip can be varied depending on various application parameters. The tip may be detachable from the applicator body, or may be an integral part of the applicator.

The replaceable tip can be composed of any of a variety of materials including polymerized materials such as plastics, foams, rubber, thermosets, films, or membranes. Additionally, the replaceable tip may be composed of materials such as metal, glass, paper, ceramics, cardboard, and the like. The replaceable tip material may be porous, absorbent, or adsorbent in nature to enhance and facilitate application of the adhesive composition. In general, the only limitation on the materials used to fabricate the tip is that the tip must be sufficiently compatible with the composition to be dispensed that undesirable effects on the composition do not prevail during contact of the composition with the tip. Thus, for example, according to embodiments of this invention where the adhesive composition is packaged as already being absorbed or adsorbed into the tip, or in direct contact with the tip, the tip is preferably made from a material that tends to stabilize, or at least does not prematurely polymerize, the adhesive monomer composition. Where the tip is made from polymer materials, the polymer material can be the same as or different from those specified above. Suitable designs for tips that may be used according to this invention are disclosed in, for example, U.S. patent application Ser. No. 08/488,411, filed Jun. 7, 1995, Ser. No. 09/069,979, filed Apr. 30, 1998, Ser. No. 09/069,875, filed Apr. 30, 1998, and Ser. No. 09/385,030, filed Aug. 30, 1999, the entire disclosures of which are incorporated herein by reference.

Furthermore, the tips of the dispensers/applicators of this invention can be provided in any of various sizes, depending on the desired use of the product. For example, a standard preferred swab size can be a rectangular shape having a size of about 1.3 cm×1.0 cm×0.64 cm. However, larger or smaller sizes can be used, where the sizes are tailored to the shape of the tip and/or the amount of adhesive material to be applied for a given application. Thus, for example, where the dispenser/applicator is intended for applications requiring a large amount of adhesive material, a larger (and/or more absorbent) tip can be used; whereas where the dispenser/applicator is intended for applications requiring only a small amount of adhesive material, a smaller (and/or less absorbent) tip can be used. Tailoring the size or absorbency/adsorbency of the tip to the amount of adhesive required can help prevent waste of adhesive material. For example, where a large tip (and large amount of adhesive) is used for a small adhesive application, the remaining adhesive in the tip is generally wasted due to premature polymerization of the adhesive in the tip.

In addition to a polymerization initiator or rate modifier, the tip may include a medicament, an anesthetic and/or other material to be applied.

The applicators/dispensers of this invention may be used to apply the polymerizable adhesive composition to a variety of substrates for the purposes of protecting, sealing, and bonding surfaces together. Suitable substrates include, but are not limited to, metals, plastics, rubbers, wood, ceramics, fabrics, cement, paper, living tissue and the like. For example, the polymerizable and/or cross-linkable material may be useful as tissue adhesives, sealants for preventing bleeding or for covering open wounds, systems for delivery of therapeutic or other bioactive agents, and other biomedical applications. They find uses in, for example, closing surgically incised or traumatically lacerated tissues; setting fractured bone structures; retarding blood flow from wounds; aiding repair and regrowth of living tissues; providing implantable matrixes for delivering bioactive agents; dressing burns; dressing skin or other superficial or surface wounds (such as abrasions, chaffed or raw skin, and/or stomatitis); protecting tissues prone to damage (e.g., as artificial calluses); and providing structural implants.

The adhesive material, in embodiments, is preferably a monomeric (including prepolymeric) adhesive composition. In embodiments, the monomer is a 1,1-disubstituted ethylene monomer, e.g., an $\alpha$-cyanoacrylate. Preferred monomer compositions of this invention, and polymers formed therefrom, are useful as tissue adhesives, sealants for preventing bleeding or for covering open wounds, and in other absorbable and non-absorbable biomedical applications. They find uses in, for example, apposing surgically incised or traumatically lacerated tissues; retarding blood flow from wounds; drug delivery; dressing burns; dressing skin or other superficial or surface wounds (such as abrasions, chaffed or raw skin, and/or stomatitis); hernia repair; meniscus repair; and aiding repair and regrowth of living tissue. Other preferred monomer compositions of this invention, and polymers formed therefrom, are useful in industrial and home applications, for example in bonding rubbers, plastics, wood, composites, fabrics, and other natural and synthetic materials.

The monomer (including prepolymeric) adhesive composition may include one or more polymerizable monomers. Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. Nos. 5,328,687 and 5,928,611 to Leung et al., U.S. patent application Ser. No. 09/430,177, filed on Oct. 29, 1999, and U.S. Pat. No. 6,183,593, which are hereby incorporated in their entirety by reference herein. Preferred monomers include 1,1-disubstituted ethylene monomers, such as $\alpha$-cyanoacrylates including, but not limited to, alkyl $\alpha$-cyanoacrylates having an alkyl chain length of from about 1 to about 20 carbon atoms or more, preferably from about 2 to about 12 or more preferably from about 3 to about 8 carbon atoms. Other suitable monomers include, but are not limited to, alkyl ester cyanoacrylate monomers, such as those disclosed in, for example, U.S. patent application Ser. No. 09/630,437, filed Aug. 2, 2000, and Ser. No. 09/919,877, filed Aug. 2, 2001, the entire disclosures of which are incorporated herein by reference.

The $\alpha$-cyanoacrylates of this invention can be prepared according to several methods known in the art. U.S. Pat. Nos. 2,721,858, 3,254,111, 3,995,641, and 4,364,876, each of which is hereby incorporated in its entirety by reference herein, disclose methods for preparing $\alpha$-cyanoacrylates.

As desired, the application according to this invention can include any of a wide variety of additional materials, either mixed into the polymerizable composition, or in a separate compartment from the polymerizable composition. Examples of suitable additional materials include, but are not limited to, plasticizing agents, thixotropic agents, thickeners, natural or synthetic rubbers, stabilizers, pH modifiers, bioactive agents, cross-linking agents, chain transfer agents, fibrous reinforcements, colorants, preservatives, formaldehyde reducing or scavenging agents, flavorants, perfumes, mixtures thereof, and the like.

The adhesive material may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), polymethylmethacrylate, polydimethylsiloxane, hexadimethylsilazane, isopropyl myristate, isopropyl palmitate, and others as listed in U.S. patent application Ser. No. 09/471,392 filed Dec. 23, 1999, the disclosure of which is incorporated in its entirety by reference herein.

The adhesive material may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. No. 4,720,513, and U.S. patent application Ser. No. 09/374,207 filed Aug. 12, 1999, the disclosures of which are hereby incorporated in their entireties by reference herein.

The adhesive material may optionally also include thickeners. Suitable thickeners may include poly (2-ethylhexyl methacrylate), poly(2-ethylhexyl acrylate) and others as listed in U.S. patent application Ser. No. 09/471,392 filed Dec. 23, 1999, and Ser. No. 09/374,207, filed Aug. 12, 1999, the disclosures of which are incorporated by reference herein in their entirety.

The adhesive material may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The adhesive material may optionally also include one or more stabilizers, preferably both at least one anionic vapor phase stabilizer and at least one anionic liquid phase stabilizer. The composition may optionally also include, in addition to or in place of the anionic stabilizers, at least one free radical stabilizer. These stabilizing agents may inhibit premature polymerization. Suitable anionic and free radical stabilizers may include those listed in U.S. patent application Ser. No. 09/471,392 filed on Dec. 23, 1999, and Ser. No. 09/099,457, filed Jun. 18, 1998, the disclosures of which are incorporated by reference herein in their entirety.

However, as described above, a particular advantage of this invention, such as in embodiments where stabilizing materials are used, is that separate stabilizers can be omitted from the composition. Thus, in embodiments, the polymerizable composition preferably does not include any, or at least substantially none, additional stabilizer.

The adhesive material may also include pH modifiers to control the rate of degradation of the resulting polymer, as disclosed in U.S. patent application Ser. No. 08/714,288, filed Sep. 18, 1996, the entire disclosure of which is hereby incorporated by reference herein in its entirety.

Adhesive materials of this invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, all to Leung et al., which are hereby incorporated herein by reference in their entireties.

To improve the cohesive strength of adhesives formed from the adhesive materials of this invention, difunctional monomeric cross-linking agents may be added to the monomer compositions of this invention. Such crosslinking agents are known. U.S. Pat. No. 3,940,362 to Overhults, which is hereby incorporated herein in its entirety by reference, discloses exemplary cross-linking agents.

The adhesive materials of this invention may further contain fibrous reinforcement and colorants such as dyes, pigments, and pigment dyes. Examples of suitable fibrous reinforcement include PGA microfibrils, collagen microfibrils, and others as described in U.S. patent application Ser. No. 09/471,392 filed on Dec. 23, 1999, the disclosure of which is incorporated by reference herein in its entirety.

The polymerizable adhesive materials useful in this invention may also further contain one or more preservatives, for prolonging the storage life of the composition. Suitable preservatives, and methods for selecting them and incorporating them into adhesive compositions, are disclosed in U.S. patent application Ser. No. 09/430,180, the entire disclosure of which is incorporated herein by reference.

In embodiments of this invention, the adhesive material and/or parts of the applicator/dispenser may contain additional materials such as a polymerization initiator, accelerator, rate-modifier, and/or cross-linking agent for initiating polymerization and/or cross-linking of the polymerizable monomer material. Such initiators, accelerators, rate-modifiers, and/or cross-linking agents can be included in the applicator tip, in the adhesive material, and/or elsewhere, as appropriate.

In embodiments of this invention, particularly where the adhesive material is not in contact with the applicator tip prior to use, it is possible to incorporate into the applicator tip additional components, such as polymerization initiators and/or accelerators, anesthetic, medicament or the like, or even any of the various additives described above with respect to the polymerizable adhesive. This is advantageous, for example, where additional initiator or accelerator may be necessary to provide the desired cure rate of the adhesive once it is applied or where additional treatment is desired. Furthermore, this is advantageous in embodiments where additional stabilizers or polymerization inhibitors must be added to the adhesive composition in the assembly, so as to overcome the "cure speed loss" that often occurs when such stabilizing agents are added.

In embodiments, the initiator or accelerator material is an initiator and/or a rate modifier for polymerization and/or cross-linking of a polymerizable monomer. As used herein, a polymerization initiator is any material that causes a monomer composition applied to a substantially dry tissue (i.e., substantially in the absence of plasma or like tissue fluids) to polymerize in less than 300 seconds at ambient temperature, for example, at approximately 21-25° C. Preferably, the initiator causes the monomer composition to polymerize in less than 150 seconds at ambient temperature, more preferably within 60, 90 or 130 seconds. As used herein, a polymerization rate modifier is any material that changes the rate at which a polymerizable monomer would polymerize in the absence of that material. Preferably, the rate modifier accelerates the rate of the polymerization reaction, although for particularly fast-acting monomers it may decelerate that rate.

The material may be applied to the applicator tip, for example, by spraying, dipping, injecting, or brushing the applicator tip with a liquid medium containing the polymerization initiator or accelerator. It is preferably applied to the tip by dipping or injecting. For example, it may be applied to the tip by pumping of the liquid medium, for example, through a syringe, onto the tip. Methods of applying the polymerization initiator or accelerator to an applicator tip are described in more detail in U.S. Pat. No. 5,928,611 to Leung and U.S. patent application Ser. No. 09/069,979, filed Apr. 30, 1998, Ser. No. 08/920,876, filed Aug. 29, 1997, and Ser. No. 09/430,177, filed Oct. 29, 1999, the entire disclosures of which is incorporated herein by reference.

Particular initiators and accelerators for particular monomers may be readily selected by one of skill in the art without undue experimentation. Control of the molecular weight distribution of the applied adhesive can be enhanced by selection of the concentration and functionality of the initiator or accelerator vis-a-vis the selected monomer. Suitable polymerization initiators and accelerators for cyanoacrylate compositions include, but are not limited to, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

In preferred embodiments, the initiator may be a bioactive material, including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt napthenate can be used as an accelerator for peroxide. Other suitable bioactive materials are disclosed in U.S. Pat. No. 5,928,611 to Leung and U.S. patent application Ser. No. 08/920,876, filed Aug. 29, 1997, Ser. No. 09/430,176 filed Oct. 29, 1999, and Ser. No. 09/430,177, filed Oct. 29, 1999, the entire disclosures of which is incorporated herein by reference.

The adhesive materials in this invention can also comprise a medicament. Inclusion of a medicament is often desirable in compositions intended for medical applications. The medicament can either be added to the monomer-containing adhesive composition prior to packaging, or, alternatively, to the applicator tip or other part. Thus, the medicament may be applied to a tissue prior to or simultaneously with application of the monomer-containing adhesive composition. In addition to serving its medicinal function, the medicament may be selected so that it functions in conjunction with the co-packaged polymerizable monomer composition to initiate polymerization of the monomer or modify (e.g., accelerate) the rate of polymerization for the monomer to form a polymeric adhesive. The proper combination of medicament and polymerizable monomer can be determined easily by one of skill in the art. The medicament is supplied in an amount that will be pharmaceutically effective when applied topically (i.e., directly to tissue).

Examples of such medicaments include, but are not limited to antibiotics, antimicrobials, antiseptics, bacteriocins, bacteriostats, disinfectants, steroids, anesthetics, fungicides, anti-inflammatory agents, antibacterial agents, antiviral agents, antitumor agents, growth promoters, and mixtures thereof.

Exemplary medicaments include, but are not limited to, quaternary ammonium halides such as benzalkonium chloride and benzethonium chloride; chlorhexidine sulfate; gentamicin sulfate; hydrogen peroxide; quinolone thioureas; silver salts, including, but not limited to, silver acetate, silver benzoate, silver carbonate, silver chloride, silver citrate, silver iodide, silver nitrate, and silver sulfate; sodium hypochlorite; salts of sulfadiazine, including, but not limited to silver, sodium, and zinc salts; and mixtures thereof.

Preferable medicaments are those that are anions or help in radical generation or that are ion pairs or are themselves radicals.

In embodiments, the medicament is preferably a quaternary ammonium halide such as alkylbenzyldimethylammonium chloride (benzalkonium chloride; BAC) with an alkyl containing 6-18 carbon atoms, its pure components, or mixtures thereof, or benzethonium chloride; or a salt of sulfadiazine, such as a silver, sodium, or zinc salt.

The medicament can have a pharmaceutical effect only at the site of application (i.e., limited to the tissue on/in which it is applied), or it can have a systemic effect (by systemic, it is not only meant that the medicament has an effect throughout the patient's body, but also at a specific site other than the site of application). In embodiments where the medicament is applied in an amount sufficient to show a systemic pharmaceutical activity, it can be absorbed, transported, or otherwise distributed to the site or sites within the patient where the pharmaceutical activity is desired, e.g., through the cardiovascular or lymph systems. The medicament may be in the form of a solid, such as a powder or a solid film, or in the form of a liquid, such as a watery, viscous, or paste-like material. The medicament may also be compounded with a variety of additives, such as surfactants or emulsifiers, and vehicles.

The polymerizable and/or cross-linkable material may be neat (no additional compounds added) or in a solvent, emulsion or suspension. Suitable solvents according to this invention include alcohol, ether alcohol, hydrocarbons, halogenated hydrocarbons, ethers, acetals, ketones, esters, acids, sulfur-or nitrogen-containing organic compounds, mixtures thereof and the like. Other suitable solvents are disclosed in U.S. Pat. No. 5,130,369 to Hughes et al. and U.S. Pat. No. 5,216,096 to Hattori et al., the entire disclosures of which are incorporated herein by reference. These solvents may be used either independently or in combination of two or more. They may also be used in conjunction with water to the extent that the polymerizable and/or cross-linkable material is dissolved or suspended in such a mixture. The total amount of solvent that may be incorporated into the polymerizable and/or cross-linkable material may be 0 to 99, preferably 1 to 50, and more preferably 3 to 25 percent by weight. Selection of the amount will, of course, depend on the desired monomer and process conditions, and amounts outside these ranges may be acceptable.

In embodiments, the monomer composition and/or its packaging are preferably sterilized. Sterilization of the monomer composition and/or its packaging can be accomplished by techniques known to one of ordinary skill in the art, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. patent application Ser. No. 09/025,472, filed on Feb. 18, 1998, the entire disclosure of which is incorporated herein by reference. The composition must show low levels of toxicity to living tissue during its useful life. In preferred embodiments of this invention, the composition is sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$. Further details of sterilization are disclosed in incorporated U.S. patent application Ser. No. 09/874,039.

It should be understood that the individual features of the various exemplary embodiments may be included or excluded as desired for a given application. As such, all possible combinations of the described features are considered to be encompassed by this invention.

Thus, while this invention has been described in terms of exemplary embodiments, it is to be understood that this invention is not to be limited to the particular configuration of these embodiments. One skilled in the art will recognize that various modifications and/or alterations of these embodiments may be made while remaining within the scope of this invention.

What is claimed is:

1. An applicator/dispenser assembly for dispensing and/or applying a polymerizable monomeric adhesive material, comprising:
    a first body portion and a second body portion, at least one of the first and second body portions being rotatable relative to the other of the first and second body portions;
    a cavity in at least one of the first and second body portions; and
    a piercing or breaking member arranged on the first body portion,
    wherein rotation of one of the first and second body portions relative to the other of the first and second body portions moves the piercing or breaking member into the cavity to rupture a container of adhesive disposed at least partially in the cavity, and
    wherein the piercing or breaking member comprises at least two opposing members such that both opposing members are moved into the cavity upon rotation of one of the first and second body portions relative to the other of the first and second body portions.

2. The applicator/dispenser of claim 1, further comprising at least one visual indicator on the first and second body portions that indicates rotation of one of the first and second body portions relative to the other of the first and second body portions from an initial position.

3. An applicator/dispenser assembly for dispensing and/or applying a polymerizable monomeric adhesive material, comprising:
    a first body portion and a second body portion, at least one of the first and second body portions being rotatable relative to the other of the first and second body portions;
    an open space at least partially in and between the first and second body portions; and
    a piercing or breaking member arranged on the first body portion,
    wherein rotation of one of the first and second body portions relative to the other of the first and second body portions moves the piercing or breaking member into the open space at least partially in and between the first and second body portions,
    the applicator/dispenser further comprising a container of adhesive material at least partially disposed within the open space at least partially in and between the first and second body portions, wherein rotation of one of the first and second body portions relative to the other of the first and second body portions moves the piercing or breaking member to rupture the container.

4. The applicator/dispenser according to claim 3, further comprising a second container having at least one opening, the second container surrounding the container of adhesive, wherein rotation of one of the first and second body portions relative to the other of the first and second body portions moves the piercing or breaking member to rupture the container containing the adhesive without breaking the second container.

5. The applicator/dispenser according to claim 4, wherein the second container includes an open hole.

6. The applicator/dispenser according to claim 3, wherein the adhesive material comprises a polymerizable monomer adhesive material.

7. The applicator/dispenser according to claim 3, wherein the adhesive material comprises a polymerizable 1,1-disubstituted ethylene monomer formulation.

8. The applicator/dispenser according to claim 3, wherein the adhesive material comprises a cyanoacrylate formulation.

9. The applicator/dispenser according to claim 4, wherein the container is formed from a material that stabilizes the polymerizable monomeric adhesive material.

10. The applicator/dispenser of claim 3, further comprising at least one visual indicator on the first and second body portions that indicates rotation of one of the first and second body portions relative to the other of the first and second body portions from an initial position.

11. The applicator/dispenser according to claim 3, further comprising a pivoting connection that movably connects the first and second body portions.

12. The applicator/dispenser according to claim 11, wherein the first and second body portions comprise a handle portion of the applicator/dispenser.

13. The applicator/dispenser according to claim 3, further comprising:
a slide assembly having a plunger portion that is at least partially disposed in the open space at least partially in and between the first and second body portions and a slide portion that is at least partially disposed outside the open space at least partially in and between the first and second body portions, the slide assembly being slidably movable to move the plunger portion toward a dispensing opening of the open space at least partially in and between the first and second body portions; and
an opening in at least one of the first and second body portions through which the slide portion of the slide assembly extends.

14. The applicator/dispenser according to claim 13, further comprising:
a container of adhesive material disposed in the open space at least partially in and between the first and second body portions between the dispensing opening of the open space at least partially in and between the first and second body portions and the plunger portion of the slide assembly, wherein movement of one of the first and second body portions relative to the other of the first and second body portions moves the piercing or breaking member to rupture the container and movement of the slide member moves the plunger portion to dispense the adhesive material from the open space at least partially in and between the first and second body portions once the container is ruptured.

15. The applicator/dispenser according to claim 14, further comprising a plug member at least partially disposed in the dispensing opening of the open space at least partially in and between the first and second body portions, the plug member being made of a material that is at least one of porous, absorbent and adsorbent in nature.

16. The applicator/dispenser according to claim 15, wherein the plug member comprises an applicator tip.

17. The applicator/dispenser according to claim 15, wherein at least one of a medicament, a polymerization initiator, a polymerization rate modifier and a stabilizer for a polymerizable monomer is in or on the plug member.

18. The applicator/dispenser according to claim 15, further comprising an applicator/dispenser tip that is attached to at least one of the plug member, the first body portion and the second body portion.

19. The applicator/dispenser according to claim 18, wherein the applicator/dispenser tip comprises one of a nozzle, a spatula, a rolling ball, a brush, and a swab.

20. The applicator/dispenser according to claim 18, wherein the applicator/dispenser tip is removable.

21. An applicator/dispenser assembly for dispensing and/or applying a polymerizable monomeric adhesive material, comprising:
a first body portion and a second body portion, at least one of the first and second body portions being rotatable relative to the other of the first and second body portions;
a cavity in at least one of the first and second body portions; and
a piercing or breaking member arranged on the first body portion,
wherein rotation of one of the first and second body portions relative to the other of the first and second body portions moves the piercing or breaking member into the cavity to rupture a container of adhesive disposed at least partially in the cavity, and
wherein at least a part of the at least one of the first and second body portions defining the cavity is formed from a material that stabilizes a polymerizable monomeric adhesive material.

22. The applicator/dispenser according to claim 21, wherein at least a part of the at least one of the first and second body portions defining the cavity is formed from a material that stabilizes a polymerizable monomeric adhesive material in the absence of a stabilizer being added to the adhesive material.

23. The applicator/dispenser according to claim 21, wherein the material that stabilizes a polymerizable monomeric adhesive material is a halogenated polymeric material.

24. The applicator/dispenser according to claim 23, wherein the halogenated polymeric material is selected from the group consisting of polyolefins, halogenated hydrocarbons, and engineered resins.

25. The applicator/dispenser according to claim 23, wherein the halogenated polymeric material is a fluorinated polymeric material.

26. An applicator/dispenser assembly for dispensing and/or applying a polymerizable monomeric adhesive material, comprising:
a first body portion and a second body portion, at least one of the first and second body portions being rotatable relative to the other of the first and second body portions;
a cavity in at least one of the first and second body portions; and
a piercing or breaking member arranged on the first body portion,
wherein rotation of one of the first and second body portions relative to the other of the first and second body portions moves the piercing or breaking member into the cavity to rupture a container of adhesive disposed at least partially in the cavity, and
wherein at least an inner surface of the cavity is coated with a material that stabilizes a polymerizable monomeric adhesive material.

27. An applicator/dispenser assembly for dispensing and/or applying a polymerizable monomeric adhesive material, comprising:
a first body portion and a second body portion, at least one of the first and second body portions being rotatable relative to the other of the first and second body portions;
a cavity in at least one of the first and second body portions; and
a piercing or breaking member arranged on the first body portion,
wherein rotation of one of the first and second body portions relative to the other of the first and second body portions moves the piercing or breaking member into the cavity to rupture a container of adhesive disposed at least partially in the cavity, and
wherein at least an inner surface of the cavity is impregnated with a material that stabilizes a polymerizable monomeric adhesive material.

28. An applicator/dispenser assembly for dispensing and/or applying a polymerizable monomeric adhesive material, comprising:
a first body portion and a second body portion, at least one of the first and second body portions being movable relative to the other of the first and second body portions;

a cavity in at least one of the first and second body portions; and a piercing or breaking member arranged on the first body portion, wherein movement of one of the first and second body portions relative to the other of the first and second body portions moves the piercing or breaking member into the cavity, and wherein the second body portion is rotatable relative to the first body portion, the applicator/dispenser further comprising a camming surface arranged on the second body portion, wherein rotation of the second body portion relative to the first body portion moves the piercing or breaking member into the cavity to rupture a container of adhesive disposed at least partially in the cavity by contacting the camming surface and the piercing or breaking member.

29. The applicator/dispenser according to claim 28, wherein the piercing or breaking member comprises at least two opposing members and the camming surface comprises at least two corresponding surfaces.

30. An applicator/dispenser assembly for dispensing and/or applying a polymerizable monomeric adhesive material, comprising:

a first body portion and a second body portion, at least one of the first and second body portions being rotatable relative to the other of the first and second body portions;

a cavity in at least one of the first and second body portions; and a piercing or breaking member arranged on the first body portion, wherein rotation of one of the first and second body portions relative to the other of the first and second body portions moves the piercing or breaking member into the cavity, the applicator/dispenser further comprising:
  a bladder disposed at least partially within the cavity, at least a portion of the bladder being flexible; and
  a container of adhesive material disposed within the bladder and at least partially located in the cavity, wherein rotation of one of the first and second body portions relative to the other of the first and second body portions moves the piercing or breaking member to rupture the container.

31. The applicator/dispenser according to claim 30, further comprising a plug member at least partially disposed in an opening of the bladder, the plug member being made of a material that is at least one of porous, absorbent and adsorbent in nature.

32. The applicator/dispenser according to claim 31, wherein the plug member comprises an applicator tip.

33. The applicator/dispenser according to claim 31, wherein at least one of a medicament, a polymerization initiator, a polymerization rate modifier and a stabilizer for a polymerizable monomer is in or on the plug member.

34. The applicator/dispenser according to claim 31, further comprising an applicator/dispenser tip that is attached to at least one of the plug member, the first body portion and the second body portion.

35. The applicator/dispenser according to claim 34, wherein the applicator/dispenser tip comprises one of a nozzle, a spatula, a rolling ball, a brush, and a swab.

36. The applicator/dispenser according to claim 34, wherein the applicator/dispenser tip is removable.

37. A kit comprising:
  at least one applicator/dispenser for dispensing and/or applying a polymerizable monomeric adhesive material comprising:
    a first body portion and a second body portion, at least one of the first and second body portions being rotatable relative to the other of the first and second body portions;
    a cavity in at least one of the first and second body portions; and
    a piercing or breaking member arranged on the first body portion,
    wherein rotation of one of the first and second body portions relative to the other of the first and second body portions moves the piercing or breaking member into the cavity; and
  a plurality of containers of adhesive material arranged to be placed at least partially in the cavity of the at least one applicator/dispenser, wherein rotation of one of the first and second body portions relative to the other of the first and second body portions moves the piercing or breaking member to rupture one of the containers that is placed at least partially in the cavity.

38. The kit according to claim 37, further comprising a plurality of removable applicator tips.

39. The kit according to claim 37, further comprising a polymerization initiator or rate modifier for the adhesive material.

40. The kit according to claim 37, wherein the adhesive material comprises a polymerizable monomer adhesive material.

41. The kit according to claim 37, wherein the adhesive material comprises a polymerizable 1,1-disubstituted ethylene monomer formulation.

42. The kit according to claim 37, wherein the adhesive material comprises a cyanoacrylate formulation.

43. The kit according to claim 37, wherein at least two of the plurality of containers contain different amounts of adhesive material.

44. The kit according to claim 37, wherein at least two of the plurality of containers contain a different adhesive material.

* * * * *